United States Patent
Hojeibane et al.

(10) Patent No.: US 7,347,869 B2
(45) Date of Patent: Mar. 25, 2008

(54) IMPLANTABLE VALVULAR PROSTHESIS

(75) Inventors: Hikmat Hojeibane, Princeton, NJ (US); David Christopher Majercak, Stewartsville, NJ (US)

(73) Assignee: Cordis Corporation, Miami Lakes, FL (US)

( * ) Notice: Subject to any disclaimer, the term of this patent is extended or adjusted under 35 U.S.C. 154(b) by 103 days.

(21) Appl. No.: 10/699,295

(22) Filed: Oct. 31, 2003

(65) Prior Publication Data

US 2005/0096735 A1    May 5, 2005

(51) Int. Cl.
*A61F 2/06* (2006.01)
(52) U.S. Cl. ..................... 623/1.24; 606/200
(58) Field of Classification Search ............... 623/1.16, 623/1.2, 1.22, 1.24, 1.26, 2.1–2.19; 606/200; 427/2.25
See application file for complete search history.

(56) References Cited

U.S. PATENT DOCUMENTS

| | | | |
|---|---|---|---|
| 4,692,164 A | 9/1987 | Dzemeshkevich et al. |
| 4,725,274 A | 2/1988 | Lane et al. |
| 4,790,843 A | 12/1988 | Carpentier et al. |
| 4,892,541 A | 1/1990 | Alonso |
| 4,969,896 A | 11/1990 | Shors |
| 5,032,128 A | 7/1991 | Alonso |
| 5,037,434 A | 8/1991 | Lane |
| 5,123,919 A | 6/1992 | Sauter et al. |
| 5,147,391 A | 9/1992 | Lane |
| 5,156,621 A | 10/1992 | Navia et al. |
| 5,163,953 A | 11/1992 | Vince |
| 5,163,955 A | 11/1992 | Love et al. |
| 5,258,023 A | 11/1993 | Reger |
| 5,326,370 A | 7/1994 | Love et al. |
| 5,326,371 A | 7/1994 | Love et al. |
| 5,344,442 A | 9/1994 | Deac |
| 5,358,518 A | 10/1994 | Camilli |

(Continued)

FOREIGN PATENT DOCUMENTS

EP    0 808 614 A    11/1997

(Continued)

OTHER PUBLICATIONS

PCT Search Report dated Aug. 10, 2003 for PCT Appl. No. PCT/US03/14148.

(Continued)

*Primary Examiner*—Brian E. Pellegrino
(74) *Attorney, Agent, or Firm*—Vincent J. Serrao

(57) ABSTRACT

The present invention relates to a medical device, and in particular, to a stent-based valve. The valve includes a radially expandable structural frame including an anchor structure having a first and a second open end, a connecting member having a first and a second end, and a cantilever valve strut having a first and a second end. The first end of the connecting member is attached to the second end of the anchor structure. The first end of the cantilever valve strut is cooperatively associated with the second end of the connecting member. The prosthetic valve further includes a biocompatible membrane assembly having a substantially tubular configuration about the longitudinal axis, with a first open and a second closed end. The first end of the membrane assembly is attached to the structural frame along the second end of the cantilever valve strut.

33 Claims, 17 Drawing Sheets

U.S. PATENT DOCUMENTS

| | | |
|---|---|---|
| 5,411,552 A | 5/1995 | Andersen et al. |
| 5,415,667 A | 5/1995 | Frater |
| 5,423,887 A | 6/1995 | Love et al. |
| 5,449,384 A | 9/1995 | Johnson |
| 5,449,385 A | 9/1995 | Religa et al. |
| 5,469,868 A | 11/1995 | Reger |
| 5,480,424 A | 1/1996 | Cox |
| 5,489,298 A | 2/1996 | Love et al. |
| 5,500,014 A | 3/1996 | Quijano et al. |
| 5,549,665 A | 8/1996 | Vessely et al. |
| 5,554,185 A | 9/1996 | Block et al. |
| 5,562,729 A | 10/1996 | Purdy et al. |
| 5,607,463 A | 3/1997 | Schwartz et al. |
| 5,607,465 A | 3/1997 | Camilli |
| 5,609,626 A | 3/1997 | Quijano et al. |
| 5,612,885 A | 3/1997 | Love |
| 5,697,382 A | 12/1997 | Love et al. |
| 5,728,152 A | 3/1998 | Mirsch, II et al. |
| 5,788,979 A * | 8/1998 | Alt et al. .................. 427/2.25 |
| 5,824,061 A | 10/1998 | Quijano et al. |
| 5,840,081 A | 11/1998 | Andersen et al. |
| 5,843,181 A | 12/1998 | Jaffe et al. |
| 5,851,232 A | 12/1998 | Lois |
| 5,855,597 A | 1/1999 | Jayaraman |
| 5,855,601 A | 1/1999 | Chuter et al. |
| 5,855,602 A | 1/1999 | Angeli |
| 5,861,028 A | 1/1999 | Angelini |
| 5,876,445 A | 3/1999 | Andersen et al. |
| 5,895,420 A | 4/1999 | Mirsch II et al. |
| 5,910,170 A | 6/1999 | Reimick et al. |
| 5,928,281 A | 7/1999 | Huynh et al. |
| 5,935,163 A | 8/1999 | Gabbay |
| 5,938,696 A | 8/1999 | Goicoechea |
| 5,957,949 A | 9/1999 | Leonhardt et al. |
| 5,997,573 A | 12/1999 | Quijano et al. |
| 6,068,638 A | 5/2000 | Makower |
| 6,071,277 A | 6/2000 | Farley et al. |
| 6,086,610 A | 7/2000 | Duerig et al. |
| 6,124,523 A | 9/2000 | Banas |
| 6,165,216 A | 12/2000 | Agathos |
| 6,168,614 B1 | 1/2001 | Andersen et al. |
| 6,200,336 B1 | 3/2001 | Pavcnik et al. |
| 6,228,112 B1 | 5/2001 | Klootz et al. |
| 6,245,100 B1 | 6/2001 | Davila et al. |
| 6,245,102 B1 | 6/2001 | Jayaramman |
| 6,283,995 B1 | 9/2001 | Moe et al. |
| 6,287,334 B1 | 9/2001 | Moll et al. |
| 6,296,662 B1 | 10/2001 | Caffey |
| 6,299,637 B1 | 10/2001 | Shaolian et al. |
| 6,315,791 B1 | 11/2001 | Karwoski et al. |
| 6,355,056 B1 | 3/2002 | Pinheiro |
| 6,368,338 B1 * | 4/2002 | Konya et al. ............... 606/200 |
| 6,375,787 B1 | 4/2002 | Lukic |
| 6,494,909 B2 | 12/2002 | Greenhalgh |
| 6,511,496 B1 * | 1/2003 | Huter et al. ................ 606/200 |
| 2002/0032481 A1 | 3/2002 | Gabbay |
| 2002/0133183 A1 | 9/2002 | Lentz |
| 2002/0138135 A1 | 9/2002 | Metzer et al. |

FOREIGN PATENT DOCUMENTS

| | | |
|---|---|---|
| EP | 0 928 606 A | 7/1999 |
| EP | 0 938 879 A | 9/1999 |
| EP | 1097728 A1 * | 5/2001 |
| EP | 1192957 | 4/2002 |
| FR | 2 788 217 A | 7/2000 |
| WO | WO 00 47136 A | 8/2000 |
| WO | WO 00 47139 A | 8/2000 |
| WO | WO 01 49213 A | 7/2001 |
| WO | WO 01 67992 A | 9/2001 |

OTHER PUBLICATIONS

PCT Search Report dated Feb. 9, 2003 for PCT Appl. No. PCT/US03/14009.

PCT Search Report dated Dec. 9, 2003 for PCT Appl. No. PCT/US03/14530.

PCT Search report dated Feb. 9, 2003 for PCT Appl. No. PCT/US03/14115.

* cited by examiner

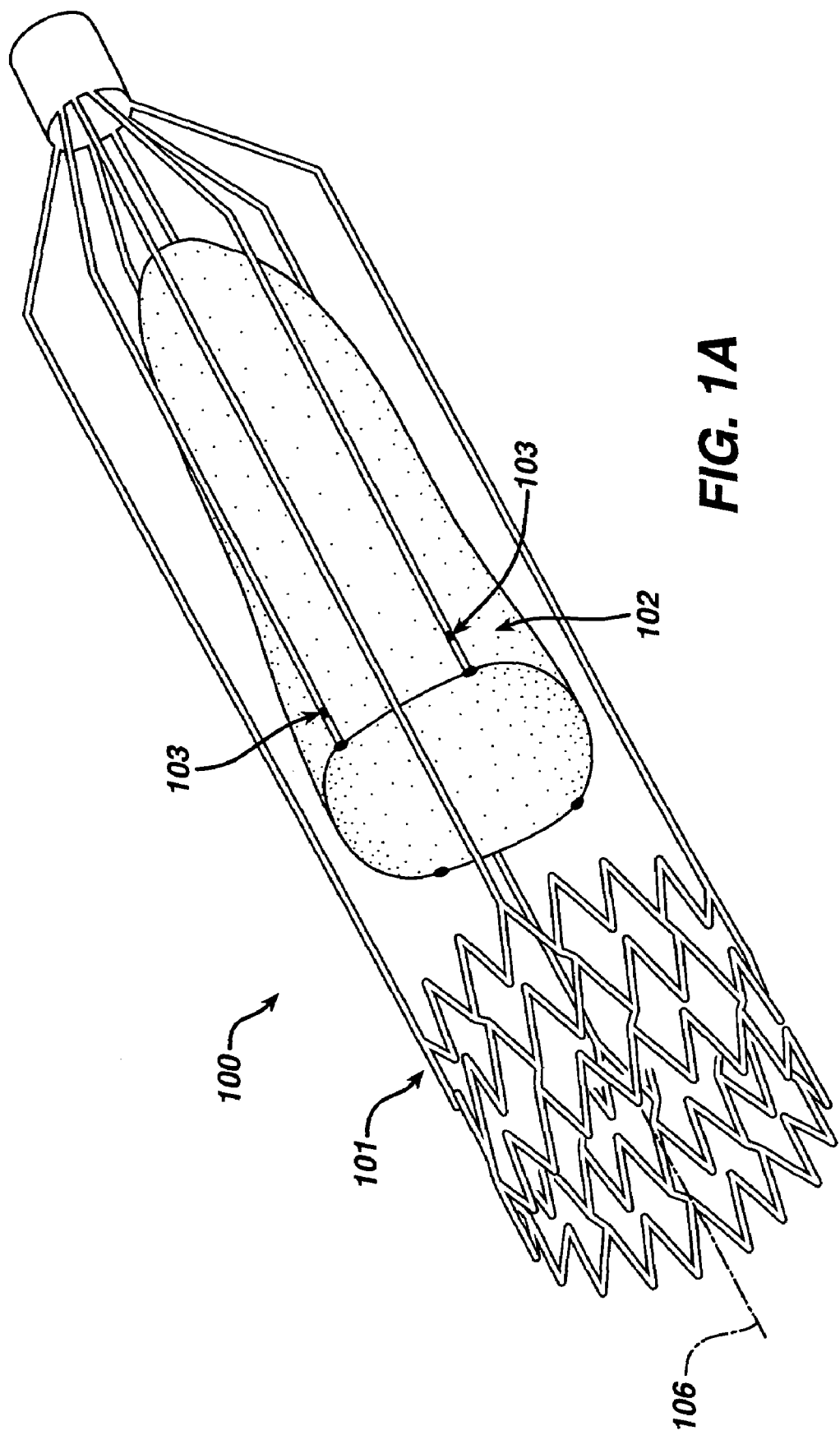

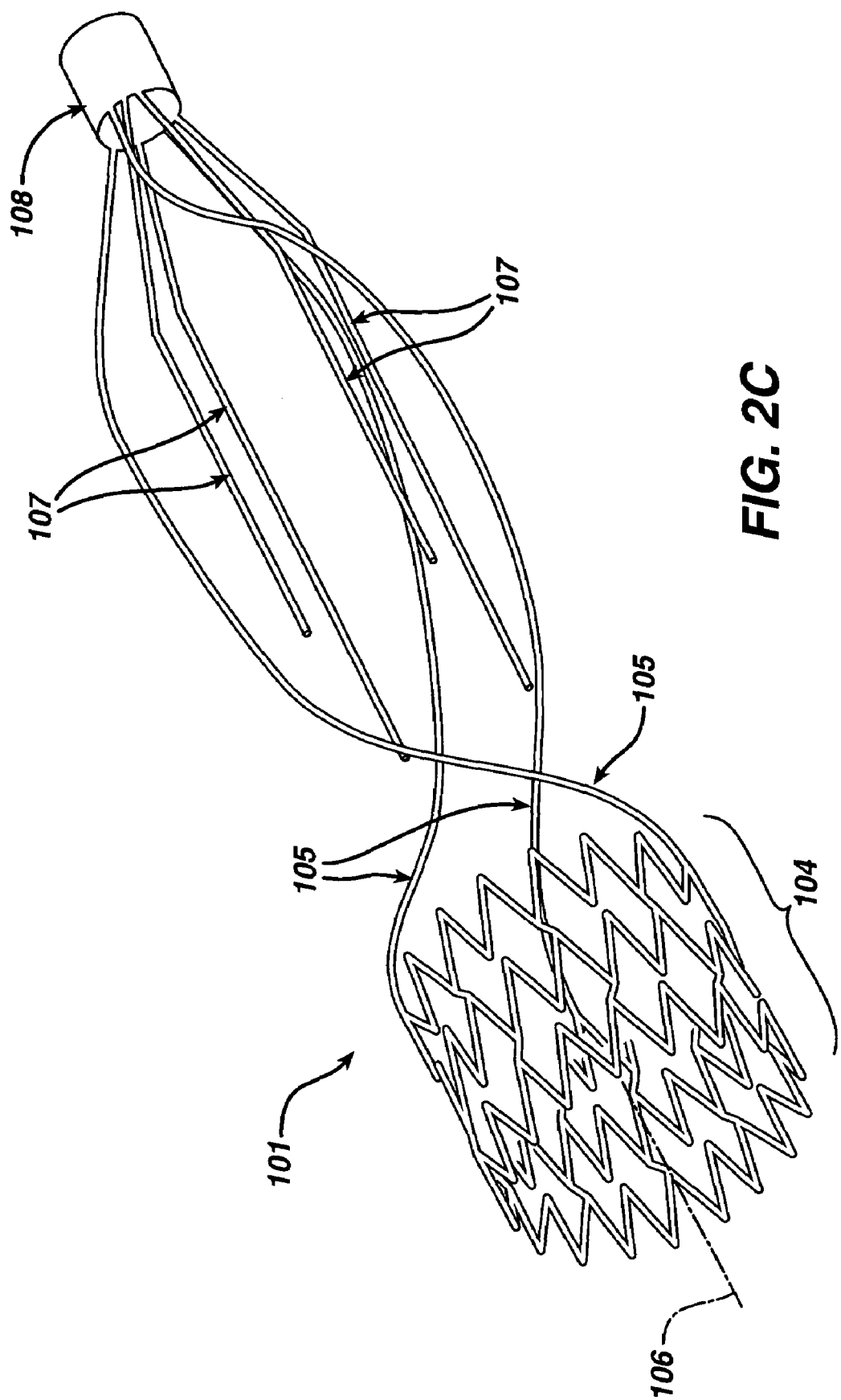

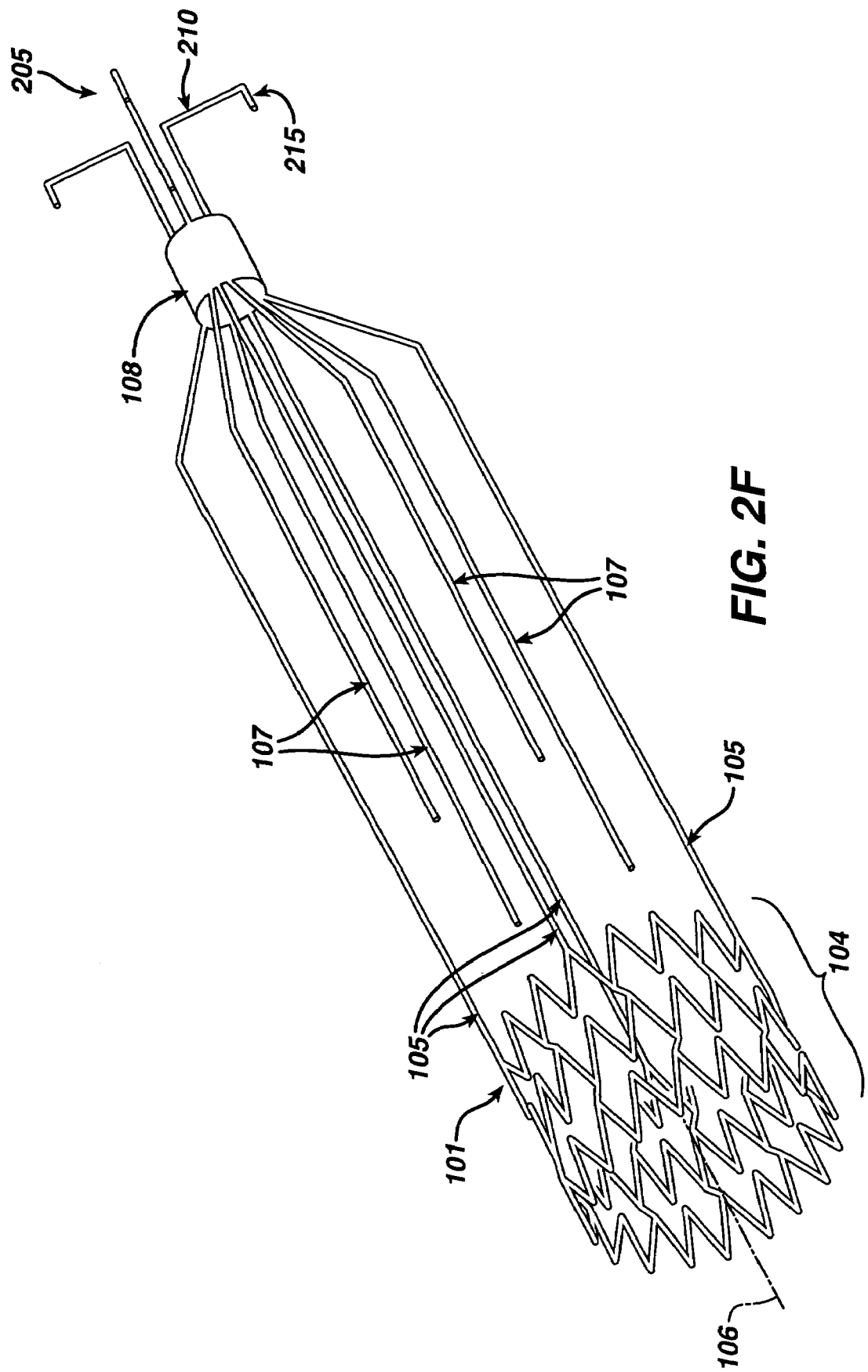

IMPLANTABLE VALVULAR PROSTHESIS

FIELD OF THE INVENTION

The present invention relates to a medical device, and more particularly to a frame based unidirectional flow prosthetic valve, and the method for fabricating such valve.

BACKGROUND OF RELATED ART

The human body has numerous biological valves that control fluid flow through body lumens and vessels. For example the circulatory system has various heart valves that allow the heart to act as a pump by controlling the flow of blood through the heart chambers, veins, and aorta. In addition, the venous system has numerous venous valves that help control the flow of blood back to the heart, particularly from the lower extremities.

These valves can become incompetent or damaged by disease, for example, phlebitis, injury, or the result of an inherited malformation. Heart valves are subject to disorders, such as mitral stenosis, mitral regurgitation, aortic stenosis, aortic regurgitation, mitral valve prolapse and tricuspid stenosis. These disorder are potentially life threatening. Similarly, incompetent or damaged venous valves usually leak, allowing the blood to improperly flow back down-through veins away from the heart (regurgitation reflux or retrograde blood flow). Blood can then stagnate in sections of certain veins, and in particular, the veins in the lower extremities. This stagnation of blood raises blood pressure and dilates the veins and venous valves. The dilation of one vein may in turn disrupt the proper function of other venous valves in a cascading manner, leading to chronic venous insufficiency.

Numerous therapies have been advanced to treat symptoms and to correct incompetent valves. Less invasive procedures include compression, elevation and wound care. However, these treatments tend to be somewhat expensive and are not curative. Other procedures involve surgical intervention to repair, reconstruct or replace the incompetent or damaged valves, particularly heart valves.

Surgical procedures for incompetent or damaged venous valves include valvuloplasty, transplantation, and transposition of veins. However, these surgical procedures provide somewhat limited results. The leaflets of some venous valves are generally thin, and once the valve becomes incompetent or destroyed, any repair provides only marginal relief.

As an alternative to surgical intervention, drug therapy to correct valvular incompetence has been utilized. Currently, however, there are no effective drug therapies available.

Other means and methods for treating and/or correcting damaged or incompetent valves include utilizing xenograft valve transplantation (monocusp bovine pericardium), prosthetic/bioprosthetic heart valves and vascular grafts, and artificial venous valves. These means have all had somewhat limited results.

What is needed is an artificial endovascular (endoluminal) valve for the replacement of incompetent biological human valves, particularly heart and venous valves. These valves may also find use in artificial hearts and artificial heart assist pumps used in conjunction with heart transplants.

SUMMARY OF THE INVENTION

The present invention relates to a medical device, and in particular, to a stent-based valve. A prosthetic valve comprises a radially expandable structural frame defining a longitudinal axis. The structural frame includes an anchor structure having a first and a second open end, a connecting member having a first and a second end, and a cantilever valve strut having a first and a second end. The first end of the connecting member is attached to the second end of the anchor structure. The first end of the cantilever valve strut is cooperatively associated with the second end of the connecting member. The prosthetic valve further includes a biocompatible membrane assembly having a substantially tubular configuration about the longitudinal axis, with a first open and a second closed end. The first end of the membrane assembly is attached to the structural frame along the second end of the cantilever valve strut.

In another embodiment of the invention, the prosthetic valve comprises a radially expandable anchor structure formed from a lattice of interconnected elements. The anchor has a substantially cylindrical configuration with a first and a second open end and a longitudinal axis defining a longitudinal direction extending there between. A connecting member and a cantilever valve strut, each having first and second ends, are also provided. The first end of the connecting member is attached to the second end of the anchor. The first end of the cantilever valve strut is cooperatively associated with the second end of the connecting member. The prosthetic valve also includes a biocompatible membrane assembly having a substantially tubular configuration with a first open and a second closed end. The first end of the membrane assembly is attached to the cantilever valve strut along the second end of the cantilever valve strut.

In still another embodiment of the present invention, the prosthetic valve comprises a radially expandable anchor structure formed from a lattice of interconnected elements. The anchor structure has a substantially cylindrical configuration with a first and a second open end and a longitudinal axis defining a longitudinal direction extending there between. A collar is provided and located proximal to the radially expandable anchor. At least one connecting member having a first and a second end is provided such that the first end of the connecting member is attached to the second end of the anchor and the second end of the connecting member is attached to the proximal collar. A cantilever valve strut is also provided. The cantilever valve strut has a first and a second end; the first end of the cantilever valve strut is attached to the proximal collar. The cantilever valve strut extends in a distal direction substantially parallel to the longitudinal axis. The prosthetic valve further comprises a biocompatible membrane assembly having a substantially tubular configuration with a first open and a second closed end. The first end of the membrane assembly is attached to the cantilever valve strut along the second end of the cantilever valve strut.

BRIEF DESCRIPTION OF THE DRAWINGS

FIG. 1A shows a perspective view of a prosthetic venous valve in the deployed state according to one embodiment of the present invention.

FIG. 2C shows a perspective view of the prosthetic venous valve structural frame having helical connecting members according to one embodiment of the present invention.

FIG. 2F shows a perspective view of the prosthetic venous valve structural frame having a proximal centering mechanism in the deployed state according to one embodiment of the present invention.

DETAILED DESCRIPTION OF THE PREFERRED EMBODIMENTS

The stent-based valves of the present invention provide a method for overcoming the difficulties associated with the treatment of valve insufficiency. Although stent based venous valves are disclosed to illustrate one embodiment of the present invention, one of ordinary skill in the art would understand that the disclosed invention can be equally applied to other locations and lumens in the body, such as, for example, coronary, vascular, non-vascular and peripheral vessels, ducts, and the like, including but not limited to cardiac valves, venous valves, valves in the esophagus and at the stomach, valves in the ureter and/or the vesica, valves in the biliary passages, valves in the lymphatic system and valves in the intestines.

In accordance with one aspect of the present invention, the prosthetic valve is designed to be percutaneously delivered through a body lumen to a target site by a delivery catheter. The target site may be, for example, a location in the venous system adjacent to an insufficient venous valve. Once deployed the prosthetic venous valve functions to assist or replace the incompetent or damaged natural valve by allowing normal blood flow (antegrade blood flow) and preventing or reducing backflow (retrograde blood flow).

A perspective view of a prosthetic venous valve in the deployed (expanded) state according to one embodiment of the present invention is shown in FIG. 1A. The prosthetic venous valve 100 comprises a structural frame 101 and a biocompatible membrane assembly 102. The membrane assembly 102 is a thin-walled biocompatible material formed into a tube with a closed end. Exemplary configurations of a closed end tube would include a tubular cup or cone shape, however one of skill in the art would understand that other configurations could also be used.

Figure 1B:
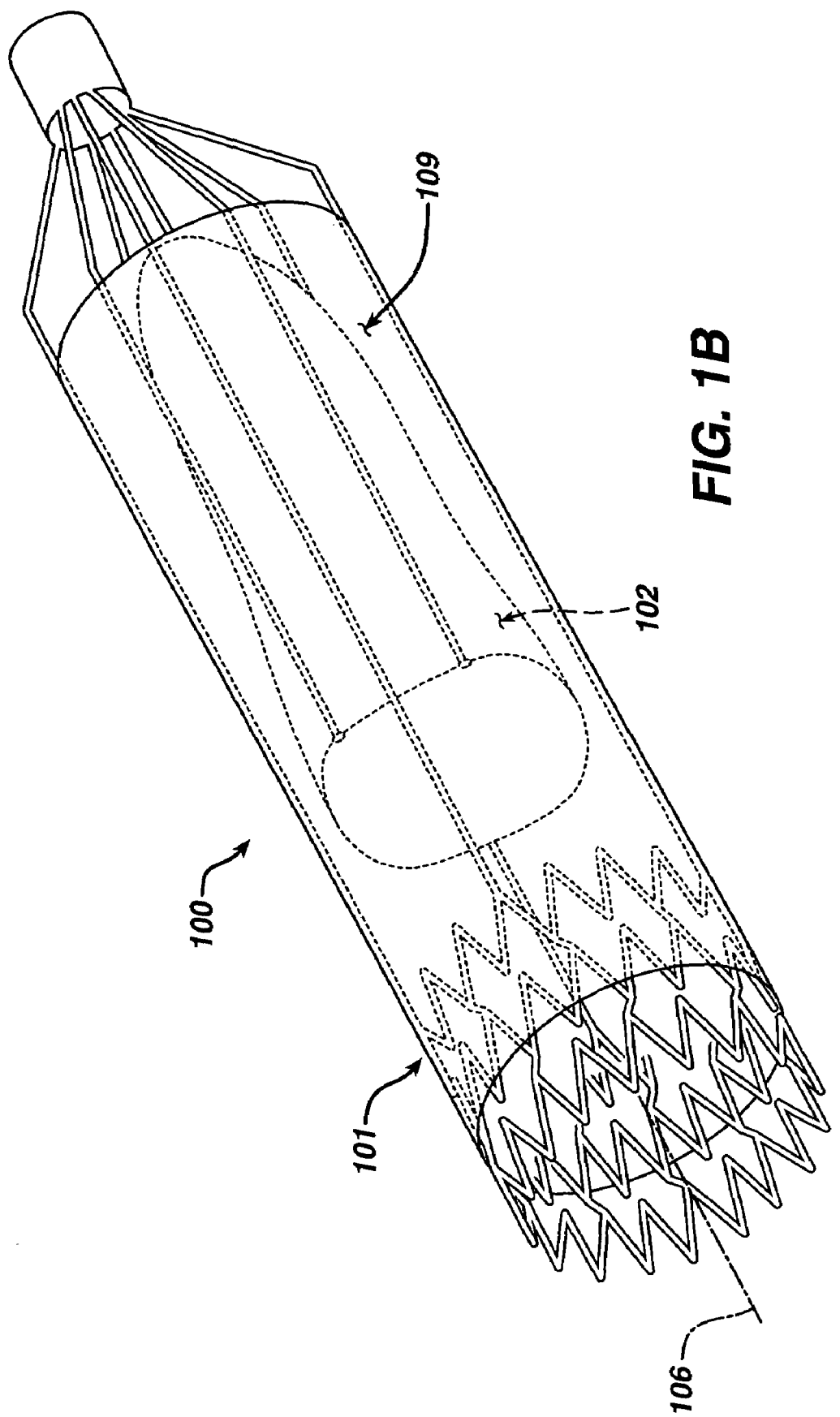
FIG. 1B shows a perspective view of a prosthetic venous valve, having a graft cover, in the deployed state according to one embodiment of the present invention.

The prosthetic venous vale 100 may also have a cover or graft material covering all or part of the structural frame 101. FIG. 1B shows a prosthetic valve 100 having a graft cover 109 according to another embodiment of the present invention. The graft 109 may be a biological material, such as a vein or small intestine submucosa (SIS) formed into a tube, but is preferably a synthetic material such as a polymer, for example an elastic or elastomeric polymer, including a fluoropolymer, fluoroelastomer, Polytetrafluoroethylene (PTFE), or a bioabsorbable material. The graft material seals off the vessel wall, e.g. in perforations and ruptures, but also in aneurysms, dissections and fistulas. The graft material may also prohibit or limit vessel wall tissue from protruding through the structural frame, occluding the vessel and/or inhibiting the operation of the membrane assembly 102.

Figure 2A:
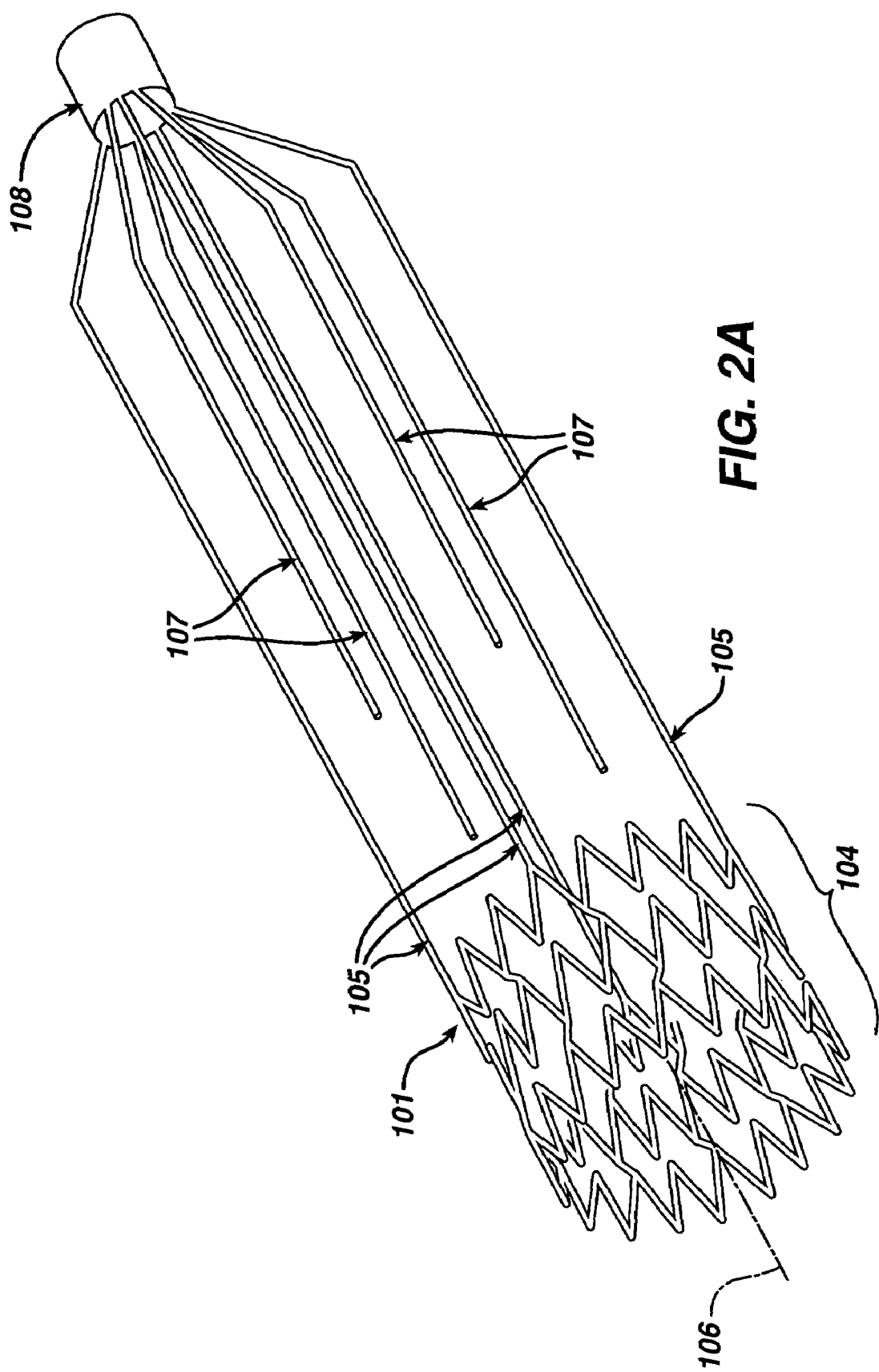
FIG. 2A shows a perspective view of the prosthetic venous valve structural frame in the deployed state according to one embodiment of the present invention.

For clarity, a perspective view of the prosthetic venous valve 100 structural frame 101 according to one embodiment of the present invention is shown in FIG. 2A. The structural frame 101 consists of an anchor structure 104 connected by at least one connecting member 105 to a proximal collar 108. In a preferred embodiment, at least two connecting members 105 are utilized. By way of example, the embodiment illustrated in FIG. 2A shows four connecting members 105.

One or more cantilever valve struts 107 extend from the proximal collar 108 in a distal (downstream) direction substantially parallel to the structural frame 101 longitudinal axis 106. The cantilever valve struts 107 are attached to biocompatible membrane assembly 102 (not shown in FIG. 2A) and further support the assembly in the open and closed positions. The proximal collar 108 serves as a connection point between the one or move valve strut members 107 and the one or more connecting members 105.

Figure 2B:
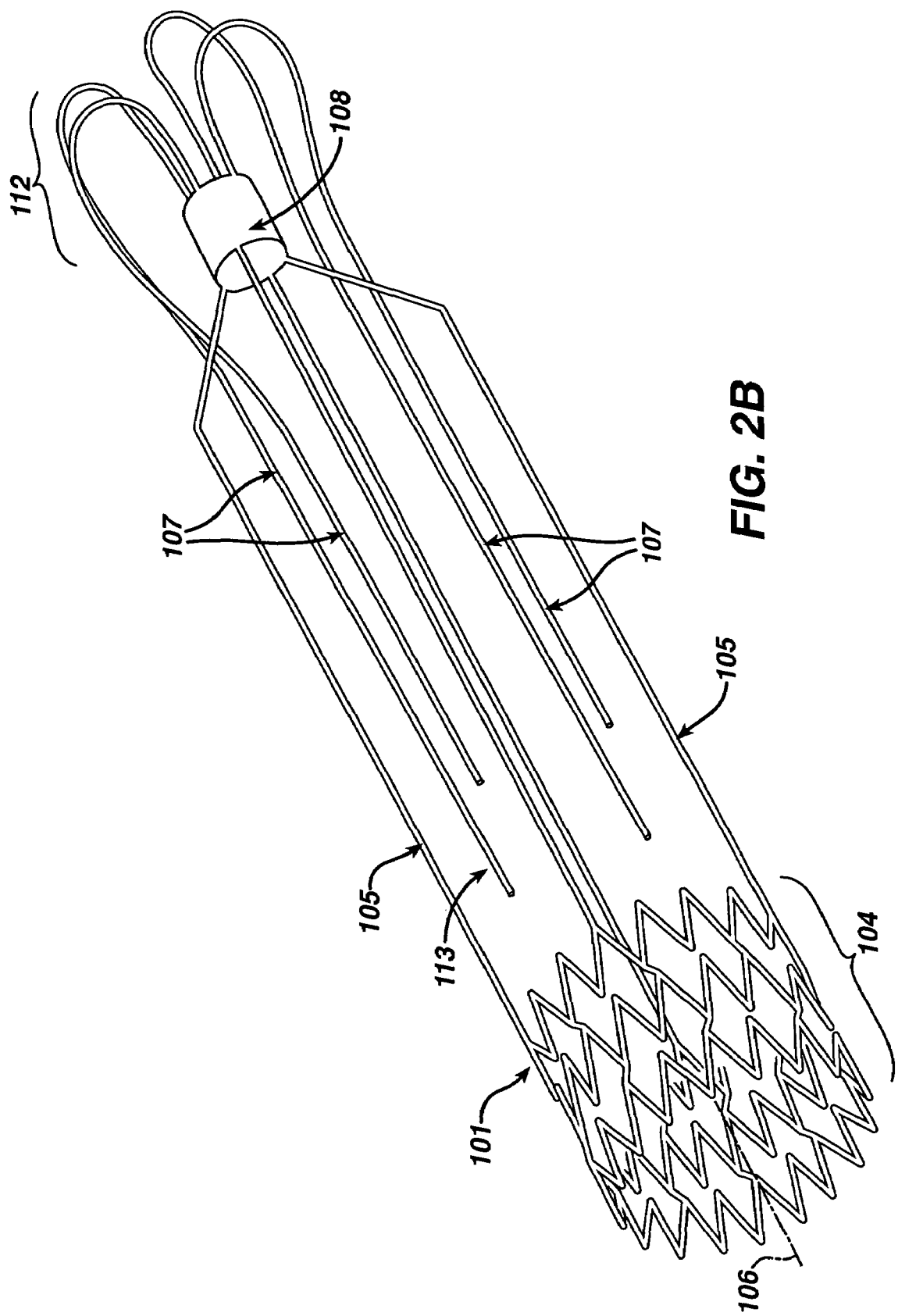
FIG. 2B shows a perspective view of the prosthetic venous valve structural frame wherein the cantilever valve struts extend from the proximal collar in a proximal direction before looping back in a distal direction according to one embodiment of the present invention.

In another embodiment of the invention illustrated in FIG. 2B, the cantilever valve struts 107 extend from the proximal collar 108 in a proximal direction before looping back in a distal direction substantially parallel to the structural frame 101 longitudinal axis 106. As disclosed in FIG. 2A, the cantilever valve struts 107 are attached to the biocompatible membrane assembly 102 (not shown in FIG. 2A or 2B) and further support the assembly in the open and closed positions. This configuration allows the cantilever valve strut 107 to be longer, increasing the flexibility of the struts 107 and helping to reduce the strains imposed in the structural frame 101 and/or membrane assembly 102.

The cantilever valve strut 107 illustrated in FIG. 2B has a loop end 112 incorporated into the proximal end and a single branch distal end 113. The loop end 112 of the valve strut 107 is attached directly to the proximal end of the proximal collar 108, and has a semi-circular configuration, substantially symmetric about its center. This configuration allows the loop end 112 to effectively reverse the direction of the cantilever valve strut 107 from a proximal direction, where it attaches to the proximal end of proximal collar 108, to a distal direction.

In a preferred embodiment, at least three cantilever valve struts 107 are utilized. In the embodiment illustrated in FIGS. 2A and 2B, four cantilever valve struts 107 are shown.

The number of cantilever valve struts 107 and connecting members 105 illustrated are not meant to limit the scope of the invention. One of skill in the art would understand that other quantities and combinations of valve struts 107 and connecting members 105 could be used and still accomplish the general intent of the invention.

In addition, the structural frame 101, particularly the connecting members 105 and/or cantilever valve struts 107 may include radiopaque markers or marker bands attached or integrated thereto. The radiopaque markers are opaque to radiation, especially to X rays and MRI, allowing the position of the structural frame 101 or its components to be viewed "in vivo". FIG. 1 illustrates marker bands 103 along the cantilever valve strut 107 members.

It should be noted that the terms proximal and distal are typically used to connote a direction or position relative to a human body. For example, the proximal end of a bone may be used to reference the end of the bone that is closer to the center of the body. Conversely, the term distal can be used to refer to the end of the bone farthest from the body. In the vasculature, proximal and distal are sometimes used to refer to the flow of blood to the heart, or away from the heart, respectively. Since the prosthetic valves described in this invention can be used in many different body lumens, including both the arterial and venous system, the use of the terms proximal and distal in this application are used to describe relative position in relation to the direction of fluid flow. As used herein, the terms upstream and downstream are relative to the normal direction of fluid flow (antegrade flow). By way of example, for venous valves, downstream connotes a direction of blood flow toward the heart. Accordingly, the use of the term proximal in the present application describes an upstream member, section or relative position regardless of its orientation relative to the body. The use of the term distal is used to describe a downstream member, section or relative position regardless of its orientation relative to the body. Similarly, the use of the terms proximal and distal to connote a direction describe upstream (retrograde) or downstream (antegrade) respectively.

In the embodiment illustrated in FIGS. 2A and 2B, the connecting members 105 are substantially linear members; connecting the stent based distal anchor 104 and the proximal collar 108. Alternatively, the connecting members 105 may be twisted in a helical fashion as they extend between the proximal collar 108 and the distal anchor 104. This alternate embodiment is illustrated in FIG. 2C. Specifically, the connection points between the connecting members 105 and the distal anchor 104, and the connecting members 105 and the proximal collar 108, are rotationally phased 180 degrees from each other to provide the helical design.

Figure 2D:
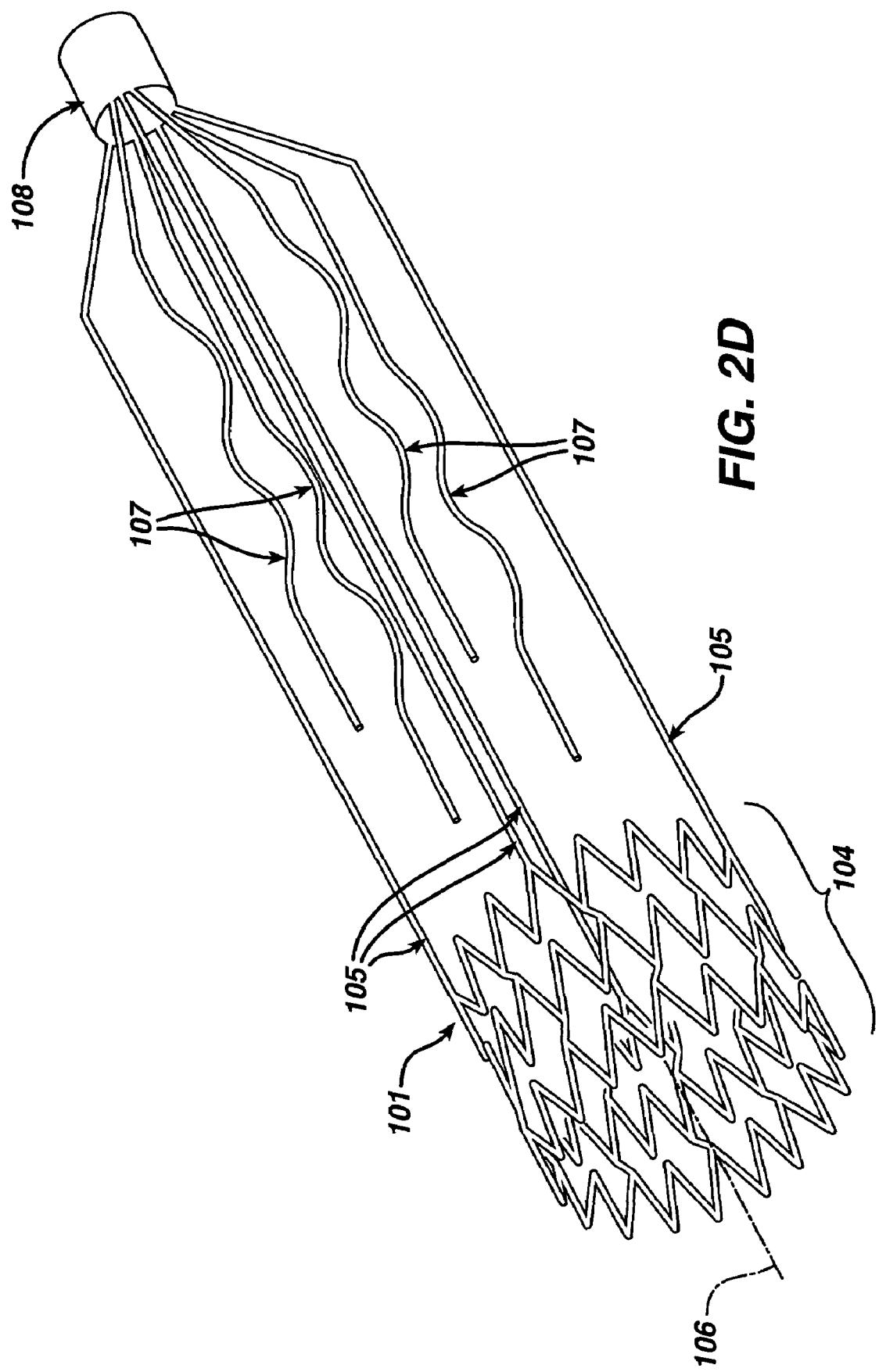
FIG. 2D shows a perspective view of the prosthetic venous valve structural frame having a sinusoidal cantilever valve strut assembly according to one embodiment of the present invention.
Figure 2E:
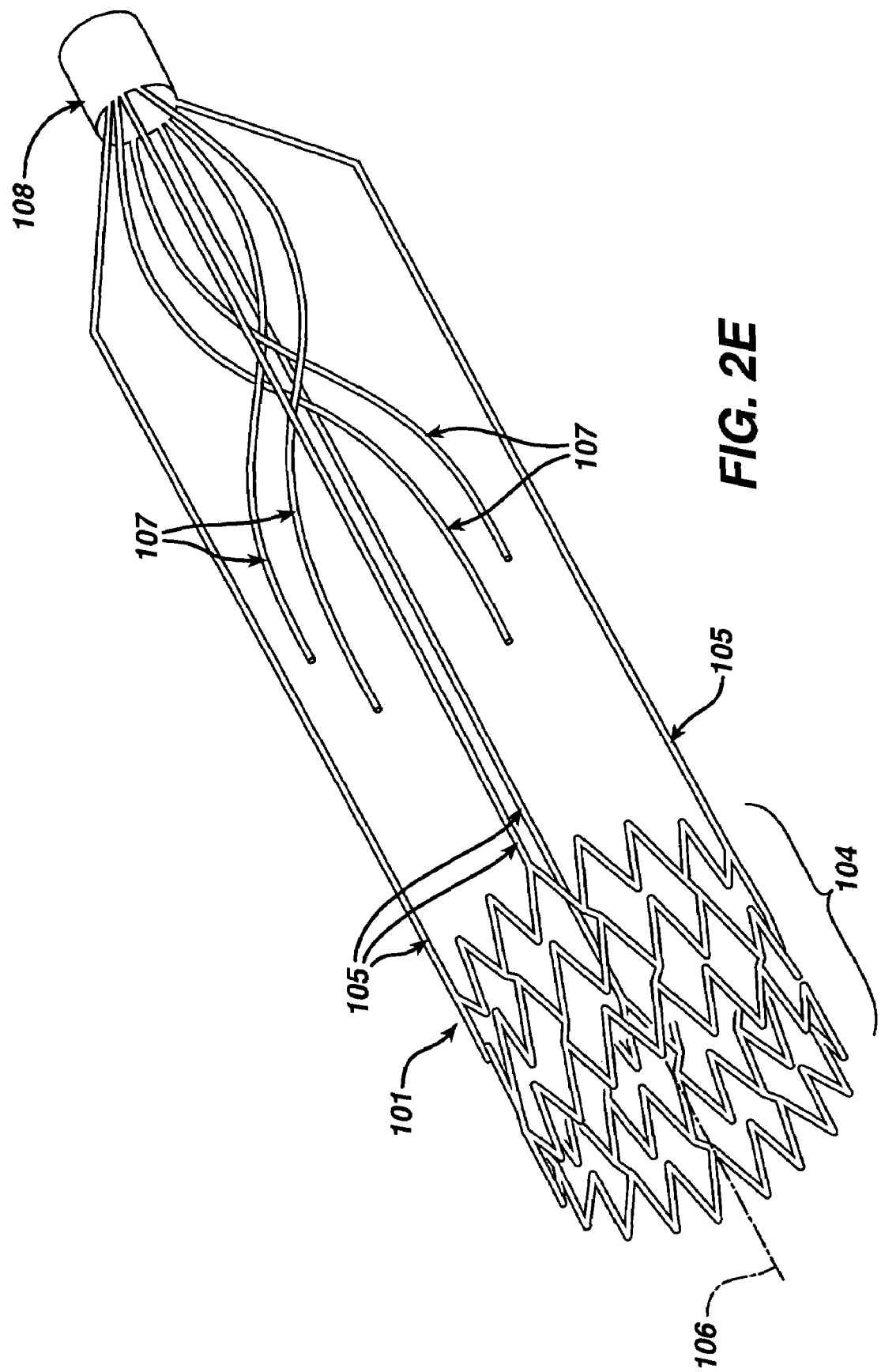
FIG. 2E shows a perspective view of the prosthetic venous valve structural frame having a helical valve strut assembly according to one embodiment of the present invention.

Similarly, the cantilever valve struts 107 are illustrated as straight members, but may take on other configurations. By way of example, FIG. 2D shows a structural frame 101 having sinusoidal cantilever valve struts 107 while FIG. 2E shows a structural frame 101 having helical cantilever valve struts 107. These various configurations may be used to change the properties of the structural frame, for example, by providing more flexibility in a particular plane or direction. Still other configurations are possible as would be understood by one of skill in the art.

The structural frame 101 could also include a secondary mechanism to center the proximal end of the frame in the body vessel or lumen. This mechanism may also provide additional anchoring to the vessel wall to further stabilize the prosthetic valve 100.

FIG. 2F shows a centering mechanism 205 incorporated into the proximal end of the structural frame 101 according to one embodiment of the present invention. The centering mechanism 205 is comprised of one or more legs 210 that extend in a substantially radial direction from the longitudinal centerline 106 to the vessel wall (not shown). In the illustrated-embodiment, 4 legs 210 are shown for the purpose of example. The legs 210 terminate with a blunt end, such as the curved bend illustrated, to reduce the possibility of the leg end perforating the vessel wall. The opposite end of the leg 210 is attached to the structural frame at or near the proximal collar 108. In the embodiment illustrated in FIG. 2F, the centering legs 210 are cut from the same tube as the remainder of the structural frame 101 such that the structural frame 101, including legs 210, is a one piece unit. Alternatively, the centering legs 210 may be separate wire units and crimped or suitably attached to the structural frame 101 at the proximal collar 108. The leg 210 may include barbs 215 on or along the end portion to further anchor the structural frame 101 to the vessel wall.

Figure 2G:
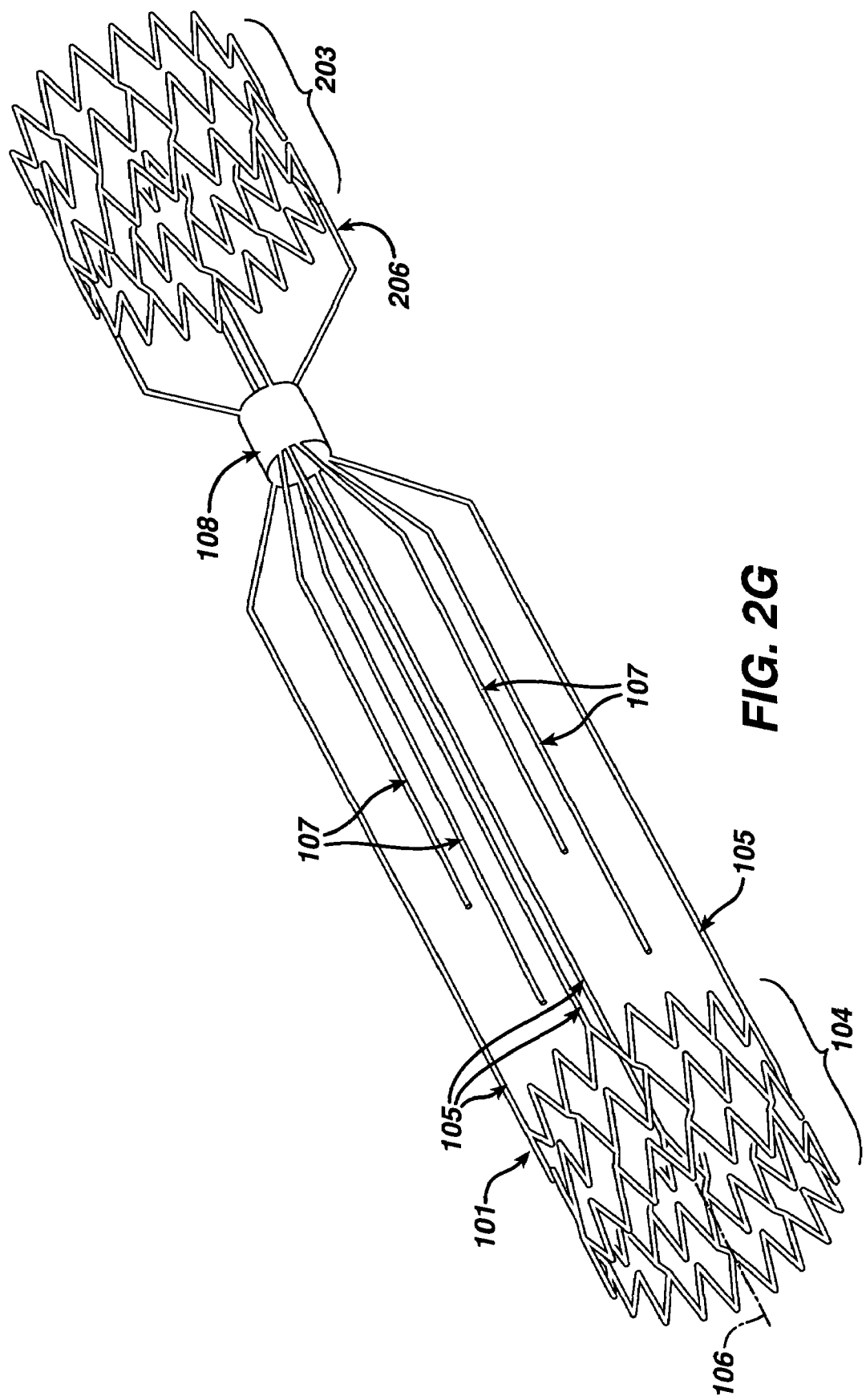
FIG. 2G shows a perspective view of the prosthetic venous valve structural frame having a distal and proximal anchor mechanism according to one embodiment of the present invention.

The structural frame 101 may also include a second anchor mechanism 203, similar to anchor 104, as shown in FIG. 2G. Aside from providing additional support and anchoring for the proximal end of the structural frame 101, the proximal anchor 203 may also act as a centering mechanism to center the proximal end of the structural frame 101 in the vessel or lumen (not shown). The proximal anchor 203 may be attached directly to the structural frame 101 at the proximal collar 108, or may be attached to the proximal collar by connecting members 206 as shown in FIG. 2G. As disclosed above, the proximal anchor 203 and connecting members 206 may be cut from the same tube as the remainder of the structural frame 101 such that the structural frame 101, including the anchor 203 and connecting members 206, is a one piece unit. Alternatively, the anchor 203 and connecting members 206 may be separate units crimped or suitably attached to the structural frame 101 at the proximal collar 108.

The materials for the structural frame 101 should exhibit excellent corrosion resistance and biocompatibility. In addition, the material comprising the structural frame 101 should be sufficiently radiopaque and create minimal artifacts during MRI.

The present invention contemplates deployment of the prosthetic venous valve 100 by both assisted (mechanical) expansion, i.e. balloon expansion, and self-expansion means. In embodiments where the prosthetic venous valve 100 is deployed by mechanical (balloon) expansion, the structural frames 101 is made from materials that can be plastically deformed through the expansion of a mechanical assist device, such as by the inflation of a catheter based balloon. When the balloon is deflated, the frame 101 remains substantially in the expanded shape. Accordingly, the ideal material has a low yield stress (to make the frame 101 deformable at manageable balloon pressures), high elastic modulus (for minimal recoil), and is work hardened through expansion for high strength. The most widely used material for balloon expandable structures 101 is stainless steel, particularly 316L stainless steel. This material is particularly corrosion resistant with a low carbon content and additions of molybdenum and niobium. Fully annealed, stainless steel is easily deformable.

Alternative materials for mechanically expandable structural frames 101 that maintain similar characteristics to stainless steel include tantalum, platinum alloys, niobium alloys, and cobalt alloys. In addition other materials, such as polymers and bioabsorbable polymers may be used for the structural frames 101.

Where the prosthetic venous valve 100 is self-expanding, the materials comprising the structural frame 101 should exhibit large elastic strains. A suitable material possessing this characteristic is Nitinol, a Nickel-Titanium alloy that can recover elastic deformations of up to 10 percent. This unusually large elastic range is commonly known as superelasticity.

The disclosure of various materials comprising the structural frame should not be construed as limiting the scope of the invention. One of ordinary skill in the art would understand that other material possessing similar characteristics may also be used in the construction of the prosthetic venous valve 100. For example, bioabsorbable polymers, such as polydioxanone may also be used. Bioabsorbable materials absorb into the body after a period of time. The period of time for the structural frame 101 to absorb may vary, but is typically sufficient to allow adequate tissue growth at the implant location to adhere to and anchor the biocompatible membrane 102.

The structural frame 101 may be fabricated using several different methods. Typically, the structural frame 101 is constructed from sheet, wire (round or flat) or tubing, but the method of fabrication generally depends on the raw material form used.

The structural frame 101 can be formed from wire using convention wire forming techniques, such as coiling, braiding, or knitting. By welding the wire at specific locations a closed-cell structure may be created. This allows for continuous production, i.e. the components of the structural frame 101, such as the anchors, to be cut to length from a long wire mesh tube. The connecting members (i.e. 206, 105) may then be directly attached to the proximal and distal anchors (i.e. 203, 104 respectively), by welding or other suitable connecting means. When this fabrication method is used, the proximal collar 108 may also be crimped over the wire frame ends (i.e. connecting members, cantilever struts, and/or centering legs) to connect the individual members together. Alternatively, the wire ends may be attached to the proximal collar 108 by welding or other suitable connecting means.

Alternatively, some or all of the complete structural frame 101 may be cut from a solid wall tube or sheet of material. Laser cutting, water-jet cutting and photochemical etching are all methods that can be employed to form the structural frame 101 from sheet and tube stock as are known in the art.

Referring to FIG. 2A for example, the structural frame 101 (including the distal anchor 104, connecting members 105, cantilever valve struts 107 and proximal collar 108) may all be cut from a solid tube eliminating the need for welding or mechanically attaching individual components together. In this embodiment, the proximal collar 108 shown is the actual solid wall tube (and remains in the pre-cut, pre-expansion size), while the remainder of the components comprising the structural frame 101 are shown in the expanded (deployed) position. As one of skill in the art would understand, the proximal collar 108 serves as a common termination point for the cantilever valve struts 107 and connecting members 105.

In other embodiments, the proximal anchor 203 or centering legs 210 may similarly be cut from the same solid wall tube as the remainder of the structural frame 101.

Alternatively, the connecting members 105 and cantilever valve struts 107 may be separate loose components, and tied to each other by the proximal collar 108. In this configuration, the proximal collar 108 acts as a connection point to connect or crimp down and hold the loose members in place. In other embodiments disclosed above, the centering legs 210, connecting members 206 and/or proximal anchor 203 may also be fabricated separate from the other structural frame 101 components, and similarly attached or crimped in place at the proximal collar 108.

As discussed above, the disclosure of various methods for constructing the structural frame 101 should not be construed as limiting the scope of the invention. One of ordinary skill in the art would understand that other construction methods may be employed to form the structural frame 101 of the prosthetic venous valve 100.

In one embodiment of the invention, the anchor 104 (and in other particular embodiments, proximal anchor 203) are stent-based structures. This configuration facilitates the percutaneous delivery of the prosthetic venous valve 100 through the vascular system in a compressed state. Once properly located, the stent-based venous valve 100 may be deployed to the expanded state.

Figure 3A:
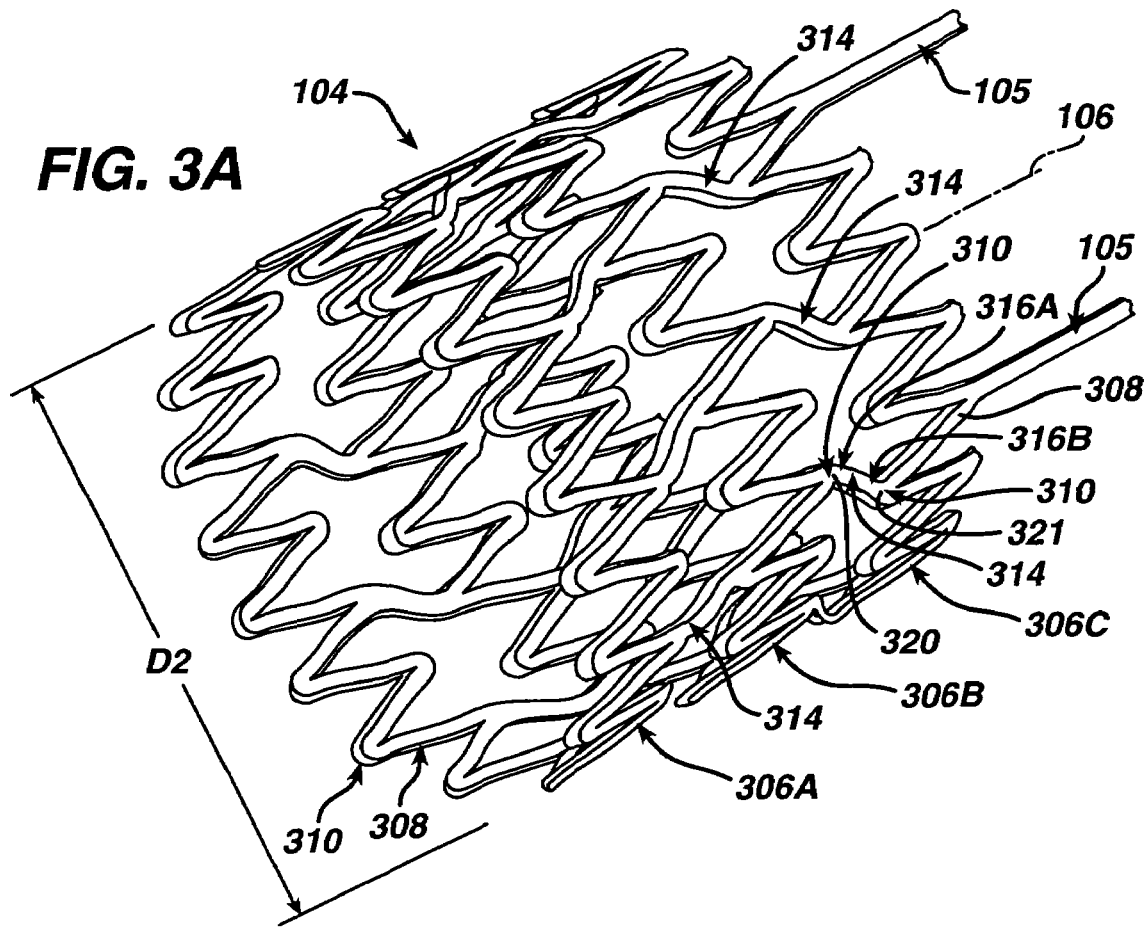
FIG. 3A shows a perspective view of the distal stent anchor having a plurality of hoop structures according to one embodiment of the present invention.

A perspective views of a typical stent-based anchor in the expanded (deployed) state is shown in FIG. 3A. Although stent anchor 104 incorporating a plurality of hoop structures (306A through 306D) is shown in the illustrated embodiment, each stent anchor may utilize a single hoop structure.

The distal stent anchor 104 (and in some embodiments proximal stent anchor 203) is comprised of a tubular configuration of structural elements having proximal and distal open ends and defining the longitudinal axis 106 extending therebetween. The stent anchor 104 has a first diameter (not shown) for insertion into a patient and navigation through the vessels, and a second diameter D2 for deployment into the target area of a vessel, with the second diameter being greater than the first diameter. The stent anchor 104, and thus the stent based venous valve 100, may be either a mechanical (balloon) or self-expanding stent based structure.

Figure 3B:
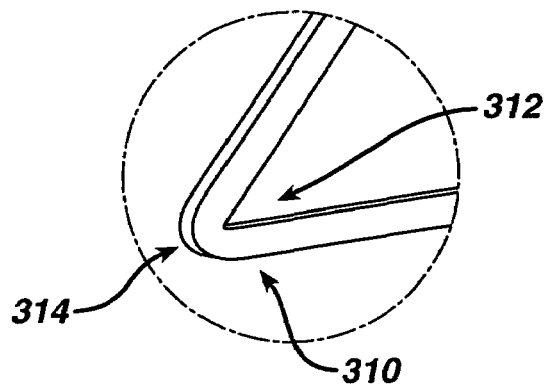
FIG. 3B shows a close-up perspective view of a loop member from the anchor having inner and outer radii according to one embodiment of the present invention.

The stent anchor 104 comprises at least one hoop structure 306 (306A through 306D are shown) extending between the proximal and distal ends. The hoop structure 306 includes a plurality of longitudinally arranged strut members 308 and a plurality of loop members 310 connecting adjacent struts 308. Adjacent struts 308 are connected at opposite ends in a substantially S or Z shaped pattern so as to form a plurality of cells. The plurality of loops 310 have a substantially semi-circular configuration, having an inter radii 312 and outer radii 314, and are substantially symmetric about their centers. The inner and outer radii 312, 314 respectively, are shown in a close-up perspective view illustrated in FIG. 3B.

In the illustrated embodiment, the distal stent anchor 104 comprises a plurality of bridge members 314 that connect adjacent hoops 306A through 306D. Each bridge member 314 comprises two ends 316A, 316B. One end 316A, 316B of each bridge 314 is attached to one loop on one hoop. Using hoop sections 306C and 306D for example, each bridge member 314 is connected at end 316A to loop 310 on hoop section 306C at a point 320. Similarly, the opposite end 316B of each bridge member 314 is connected to loop 310 on hoop sections 306D at a point 321.

As described earlier, although a Z or S shaped pattern stent anchor is shown for the purpose of example, the illustration is not to be construed as limiting the scope of the invention. One of ordinary skill in the art would understand that other stent geometries may be used.

Figure 3C:
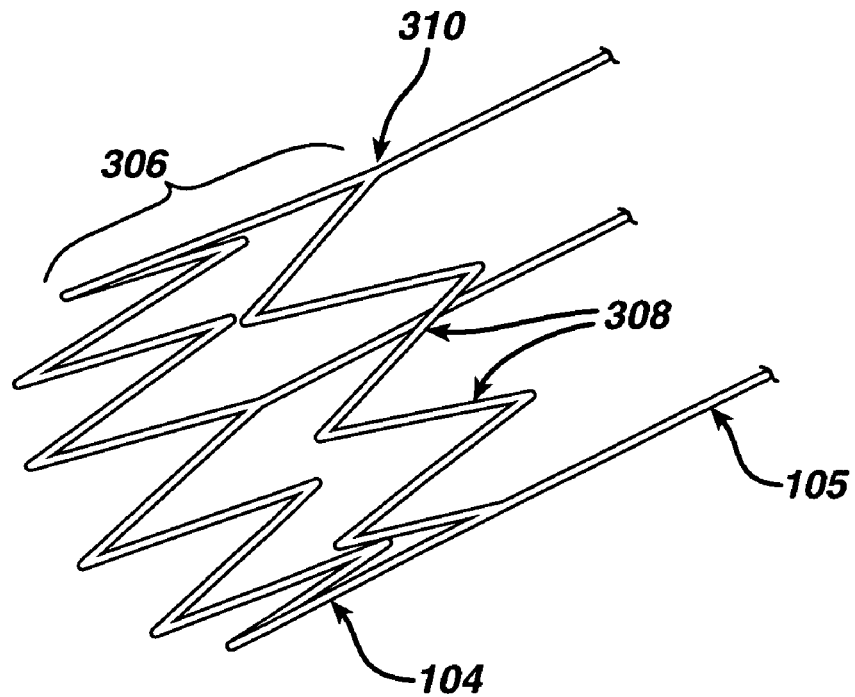
FIG. 3C illustrates a single hoop anchor having three connecting members connected to the proximal end of the distal anchor at the outer radii of the inflection point of the loop members.

The connecting member 105 may be connected to the distal anchor 104 at various points along the structure. As illustrated in FIG. 3A, the connecting members 105 are connected to the proximal end of the distal anchor 104 at the inflection point of the loop members 310, particularly at the outer radii 314 of the inflection point of loop members 310. Similarly, FIG. 3C illustrates a single hoop anchor 104 having three connecting members 105 connected to the proximal end of the distal anchor 104 at the outer radii 314 of the inflection point of loop members 310.

Preferably the connecting members 105 are connected to the inflection point of loop members 310 at evenly spaced intervals along the circumference of the tubular anchor 104. This configuration facilitates the radial expansion of the prosthetic valve from the collapsed (delivered) state to the expanded (deployed) state, and provides a substantially symmetrical valve configuration.

Figure 3D:
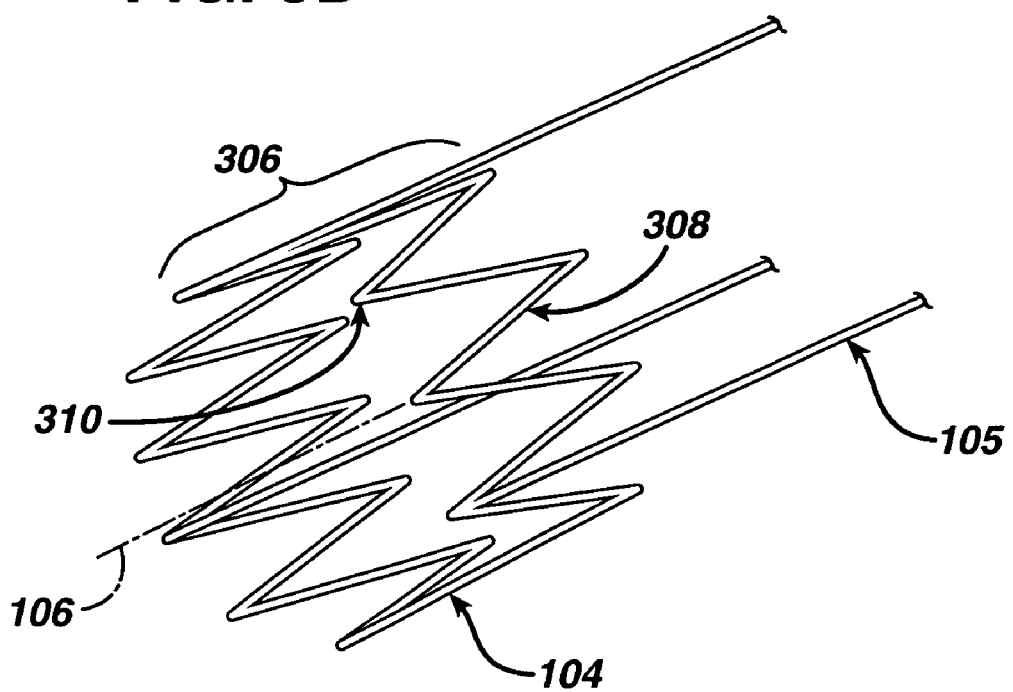
FIG. 3D illustrates a single hoop anchor having three connecting members connected to the proximal end of the distal anchor at the inner radii of the inflection point of the loop members.

Alternatively, the connecting members 105 may be connected to the proximal end of the distal anchor 104 at the inner radii 312 of the inflection point of loop member 310. This configuration is illustrated in FIG. 3D. FIG. 3D also illustrates a partial perspective view of the structural frame 101 having a single hoop structure 306 and three connecting members.

Figure 3E:
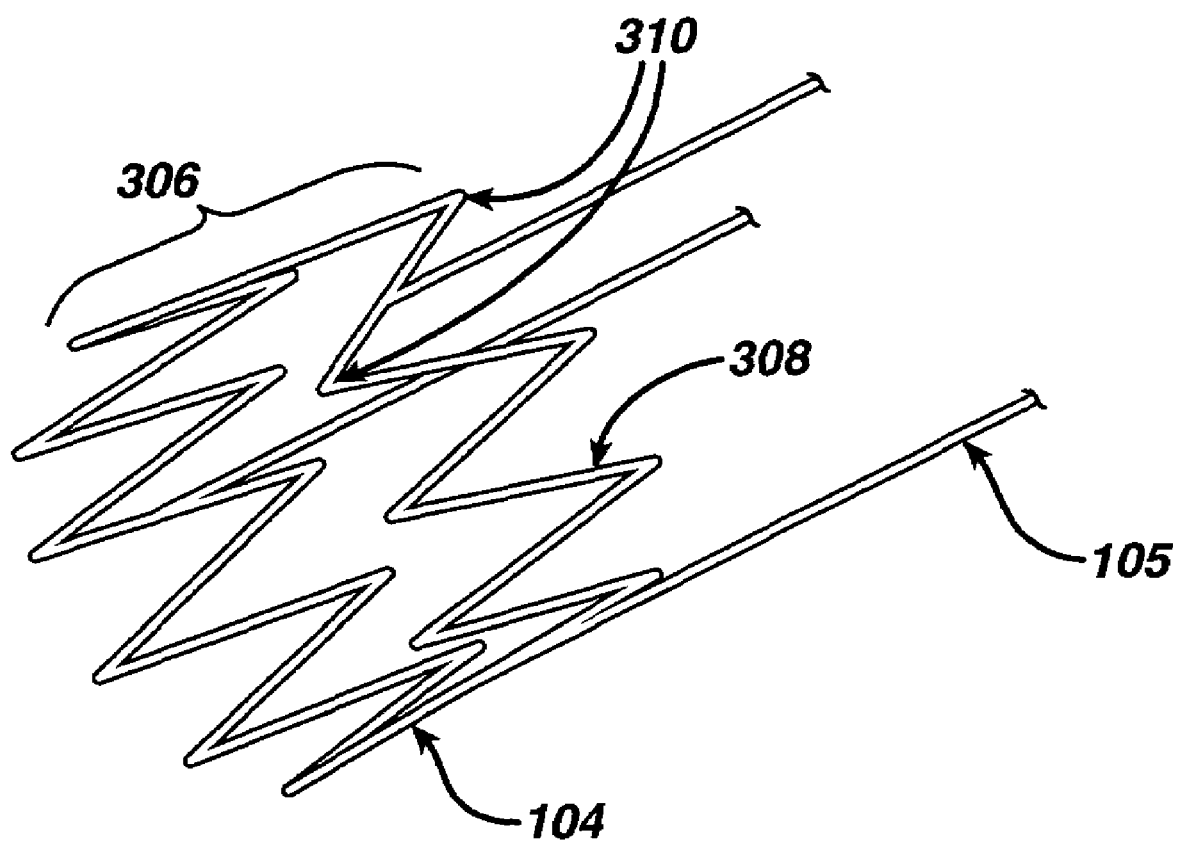
FIG. 3E illustrates a single hoop anchor having three connecting members connected to the proximal end of the distal anchor along the strut members connecting the loop members.

In still a further embodiment, the connecting members 105 may be connected along the strut members 308 of the distal anchor 104 as shown in FIG. 3E.

In any of the above described configurations, the connections between the connecting members 105 and the anchor 104 may be made at every inflection point around the circumference of the structure; or alternatively, at a subset of the inflection points around the circumference of the structure. In other words, connected inflection points alternate with unconnected inflection points in some defined pattern.

The distal anchor 104 secures the prosthetic valve 100 to the inside wall of a body vessel such as a vein, and provide anchor points for the connecting members 105. Once deployed in the desired location, the anchor 104 will expand to an outside diameter slightly larger that the inside diameter of the native vessel (not shown) and remain substantially rigid in place, anchoring the valve assembly to the vessel. The connecting members 105 preferably have an inferior radial stiffness, and will conform much more closely to the native diameter of the vessel, facilitating the operation and stability of the prosthetic valve 100.

The stent anchor may also have spurs or barbs (not shown) protruding from its proximal or distal end to further assist anchoring the prosthetic valve.

The membrane assembly 102 is formed from a flexible membrane-like biocompatible material shaped into a tubular structure with a closed end. Exemplary embodiments would include a cup or cone shaped tube. The flexible membrane may be elastic, semi-elastic or display little or no elasticity. One of skill in the art would appreciate that there are many different methods, some known in the art, which may be employed to manufacture the membrane assembly 102 from this material.

The biocompatible material may be a biological material, such as a vein or small intestine submucosa (SIS) formed into a cup or pocket, but is preferably a synthetic material such as a polymer, for example an elastic or elastomeric polymer, including a fluoropolymer, fluoroelastomer, or a bioabsorbable material, such as a bioabsorbable polymer or bioabsorbable elastomer. Bioabsorbable materials may allow cells to grow and form a tissue membrane (or valve flaps) over the bioabsorbable membrane. The bioabsorbable membrane then absorbs into the body, leaving the tissue membrane and/or flaps in place to act as a new natural tissue valve.

The membrane material may also be made from other synthetics, such as thin metallic materials or membranes.

The membrane must be strong enough to resist tearing under normal use, yet thin enough to provide the necessary flexibility that allows the biocompatible membrane assembly 102 to open and close satisfactorily. To achieve the necessary flexibility and strength of the membrane assembly 102, the synthetic material may be, for example, reinforced with a fiber, such as an electrostatically spun (ESS) fiber, or formed from a porous foam, such as ePTFE, or a mesh.

Particular ESS fibers suitable for the spinning process include fluoropolymers, such as a crystalline fluoropolymer with an 85/15% (weight/weight ratio) of vinylidene fluoride/hexafluoropropylene (VDF/HFP). Solvay Solef® 21508 and Kynarflex 2750-01 are two such examples. However, one of skill in the art would understand that any material possessing the desired characteristics may be used, including, for example: bioabsorbable polymers, such as polyglycolic acid, polylactic acid, poly (paradioxanone), polycaprolactone, poly (trimethylenecarbonate) and their copolymers; and semicrystalline bioelastomers, such as 60/40% (weight/weight ratio) of polylactic acid/polycaprolactone (PLA/PCL), 65/35 (weight/weight ratio) of polyglycolic acid/polycaprolactone (PGA/PCL), or nonabsorbable siliconized polyurethane, non-siliconized polyurethanes, siliconized polyureaurethane, including siliconized polyureaurethane end capped with silicone or fluorine end groups, or natural polymers in combination thereof. It should be noted that poly(trimethylenecarbonate) can not be spun as a homopolymer.

The ESS formed membrane assembly 102 may also be coated with a polymer solution, such as fluoroelastomer. The coating process may take place before the membrane assembly is attached to the cantilever valve struts 107, or after the membrane assembly 102 and cantilever valve struts 107 are assembled.

The coating process may act to encapsulate and attach at least a portion of the spun ESS reinforcement fiber to the cantilever valve strut 107 assembly. It should be noted that in some embodiments of the invention, some movement between the membrane assembly 102 and the cantilever valve strut 107 assembly is desired. Accordingly, not all of the ESS fiber spun cantilever valve strut 107 assembly may be coated.

The coating process may also remove some porosity of the membrane material. However, it may be desirable to maintain some porosity in particular embodiments to promote biological cell grown on and within the membrane tubular structure.

The coating solution preferably comprises a polymer put into solution with a solvent. As the solvent evaporates, the polymer comes out of solution forming the coating layer. Accordingly, for the process to work properly, the solvent used in the coating solution should not dissolve or alter the ESS fibers being coated. By way of example, a coating solution of 60/40% VDF/HFP in methanol (methanol being the solvent) has been found to be a suitable solution for coating an ESS fiber comprised of 85/15% VDF/HFP.

In one embodiment of the invention, the polymer comprising the coating is Daikin's Dai-El G701BP, which is a 60/40% VDF/HFP. In addition, Daikin's Dai-El T630, a thermoplastic elastomer based on vinylidene fluoride/hexafluoropropylene/tetrafluoroethylene (VDF/HFP/TFE) can also be used. Again, one of ordinary skill in the art would understand that other materials having suitable characteristics may be used for the coating, for example, other polymers, such as siliconized polyurethane, including Polymer Technology Group's Pursil, Carbosil, Purspan and Purspan F.

In another embodiment the membrane assembly is made from a micro-cellular foam or porous material, such as, for example an ePTFE membrane.

In this embodiment, the membrane assembly 102 is fabricated from a polymer material that can be processed such that it exhibits an expanded cellular structure, preferably expanded Polytetrafluoroethylene (ePTFE). The ePTFE tubing is made by expanding Polytetrafluoroethylene (PTFE) tubing, under controlled conditions, as is well known in the art. This process alters the physical properties that make it satisfactory for use in medical devices. However, one of ordinary skill in the art would understand that other materials that possess the necessary characteristics could also be used.

The micro-cellular foam or porous material (preferably expanded Polytetrafluoroethylene (ePTFE)) may be coated with a polymer. The polymer can be coated on the inside or outside surface of the ePTFE tube. Alternatively, the polymer may be coated on the inside and outside of the ePTFE tube.

In a preferred embodiment of the invention, the polymer comprising the coating includes Daikin's Dai-El T630, a thermoplastic elastomer based on vinylidene fluoride/hexafluoropropylene/tetrafluoroethylene (VDF/HFP/TFE) and blends thereof. Again, one of ordinary skill in the art would understand that other materials having suitable characteristics may be used for the coating, for example, other polymers, such as siliconized polyurethanes and blends thereof, including Polymer Technology Group's Pursil, Carbosil, Purspan and Purspan F.

The membrane assembly 102 formed from the micro-cellular foam or porous membrane may also be coated with a fluoroelastomer. In one embodiment of the invention, the coating is Daikin G701BP, which is a 60/40% VDF/HFP. Again, one of ordinary skill in the art would understand that other materials having suitable characteristics might be used for the coating, for example, other polymers, such as siliconized polyurethane.

The coating process may take place before the membrane assembly is attached to the cantilever valve struts 107, or after the membrane assembly 102 and cantilever valve struts 107 are assembled. The coating process may act to encapsulate and attach at least a portion of the micro-cellular foam or porous membrane tube to the cantilever valve strut 107 assembly.

Some post processing of the membrane assembly 102 may also take place to achieve particular desired characteristics or configurations. This may includes creating the final closed cup or cone shape of the membrane assembly 102 if needed. In addition, post processing may change the characteristics of the membrane assembly 102 by thickening or thinning the membrane in particular locations. Thickening the membrane may add rigidity and reinforcement to a particular area. Thinning the membrane may make the membrane more pliable, which is a desirable characteristic. Still other post processing procedures may change the physical shape of the membrane assembly 102, for example, by forming loop collars (such as loop collars 605 in FIGS. 6A through 6C) along the distal edge of membrane assembly 102.

The thickness of the synthetic valve membrane assembly 102 is dependent on the size, type and location of the prosthetic valve. For venous valves applications a polymeric membrane assembly 102 having a thickness of between 12 µm and 100 µm and preferably between 25 µm and 50 µm has been found to be acceptable.

In one embodiment of the invention, the membrane assembly 102 is placed on the inside of the cantilever valve struts 107. However, in other embodiments, the membrane assembly may be placed over the cantilever valve struts 107.

Figure 4A:
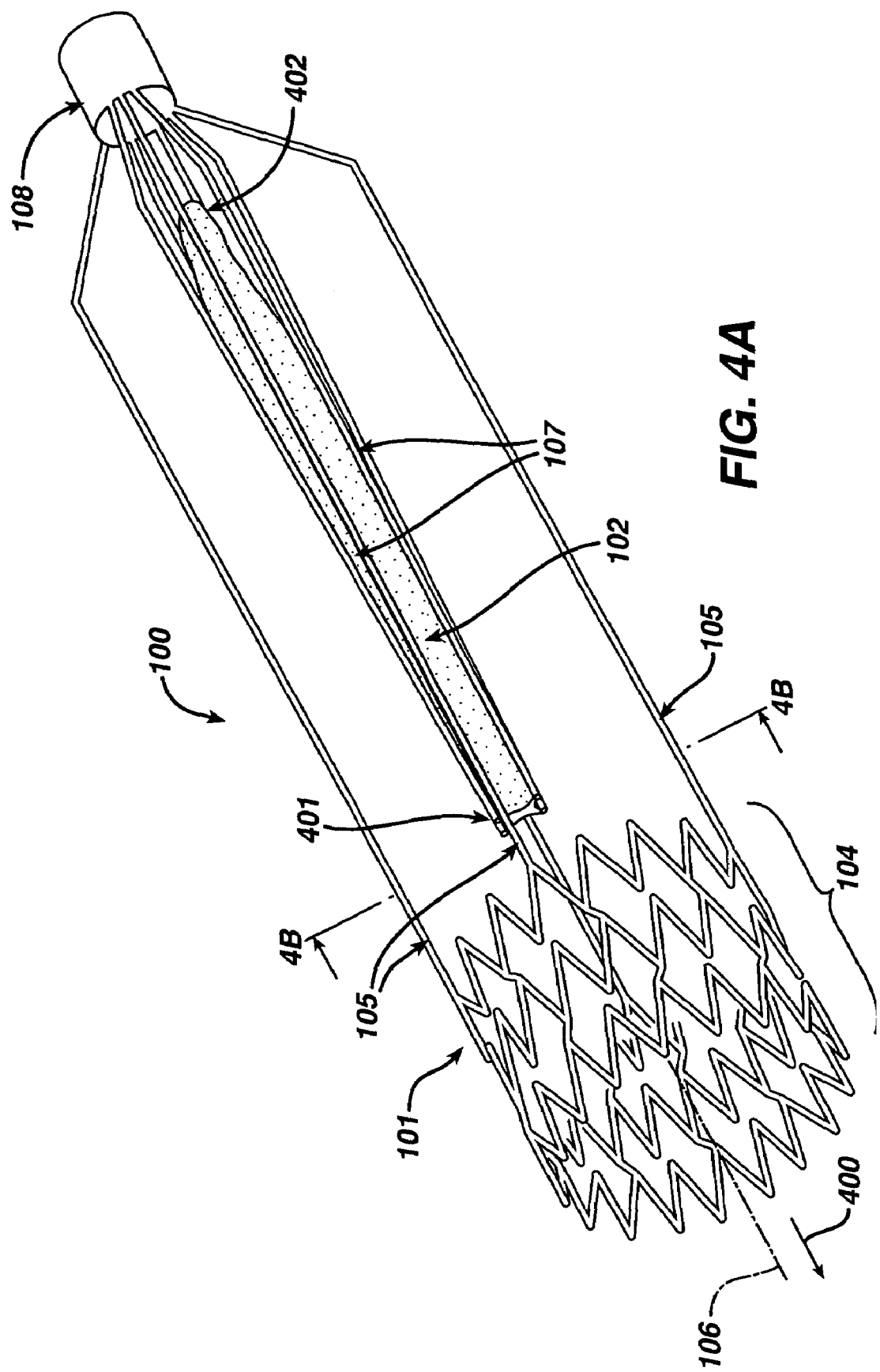
FIG. 4A is a perspective view illustrating one embodiment of the deployed prosthetic venous valve assembly in the open position.
Figure 4B:
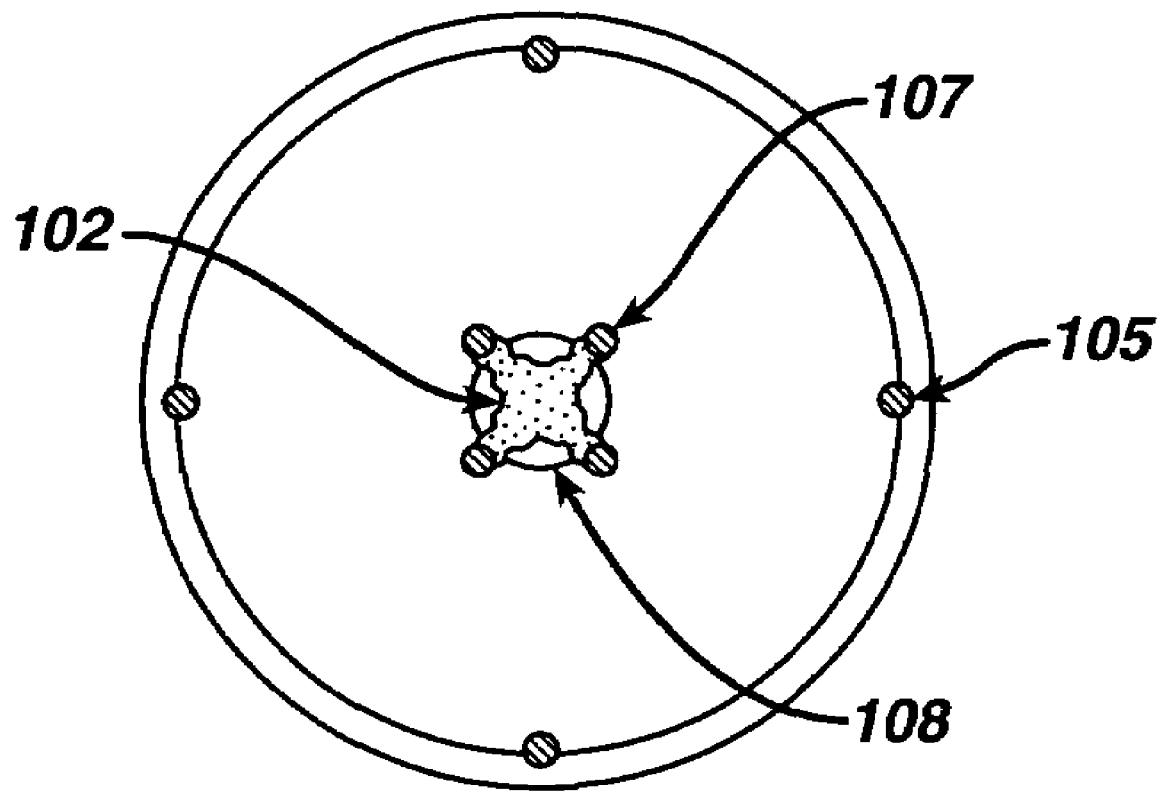
FIG. 4B is a section view illustrating one embodiment of the deployed prosthetic venous valve assembly in the open position.

FIGS. 4A and 4B are perspective and section views, respectively, illustrating one embodiment of the expanded (deployed) prosthetic venous valve assembly 100 in the open position. In this embodiment, the term open means that the prosthetic venous valve 100 is configured to allow antegrade blood flow 400 to pass through the valve. To accomplish this, the membrane assembly 102 is in a substantially collapsed position.

The flexible membrane like biocompatible material is formed into a tubular cup or cone (membrane assembly 102) and suitably attached to the cantilever valve struts 107 of the structural frame 101. The membrane assembly 102 has a first (distal) and second (proximal) ends 401, 402 respectively.

The first end 401 of the membrane assembly 102 is located at the distal end of the cantilever valve strut 107 near the proximal end of the distal anchor 104. The membrane assembly extends proximally along the cantilever valve strut 107 and terminates at the second end 402 with a closed cup or cone end.

The illustrated embodiment shows a valve having a single cone or cup, and may be considered a monocusp design. However, other configurations using more than a single cup or cone are also contemplated by the present invention.

Figure 5A:
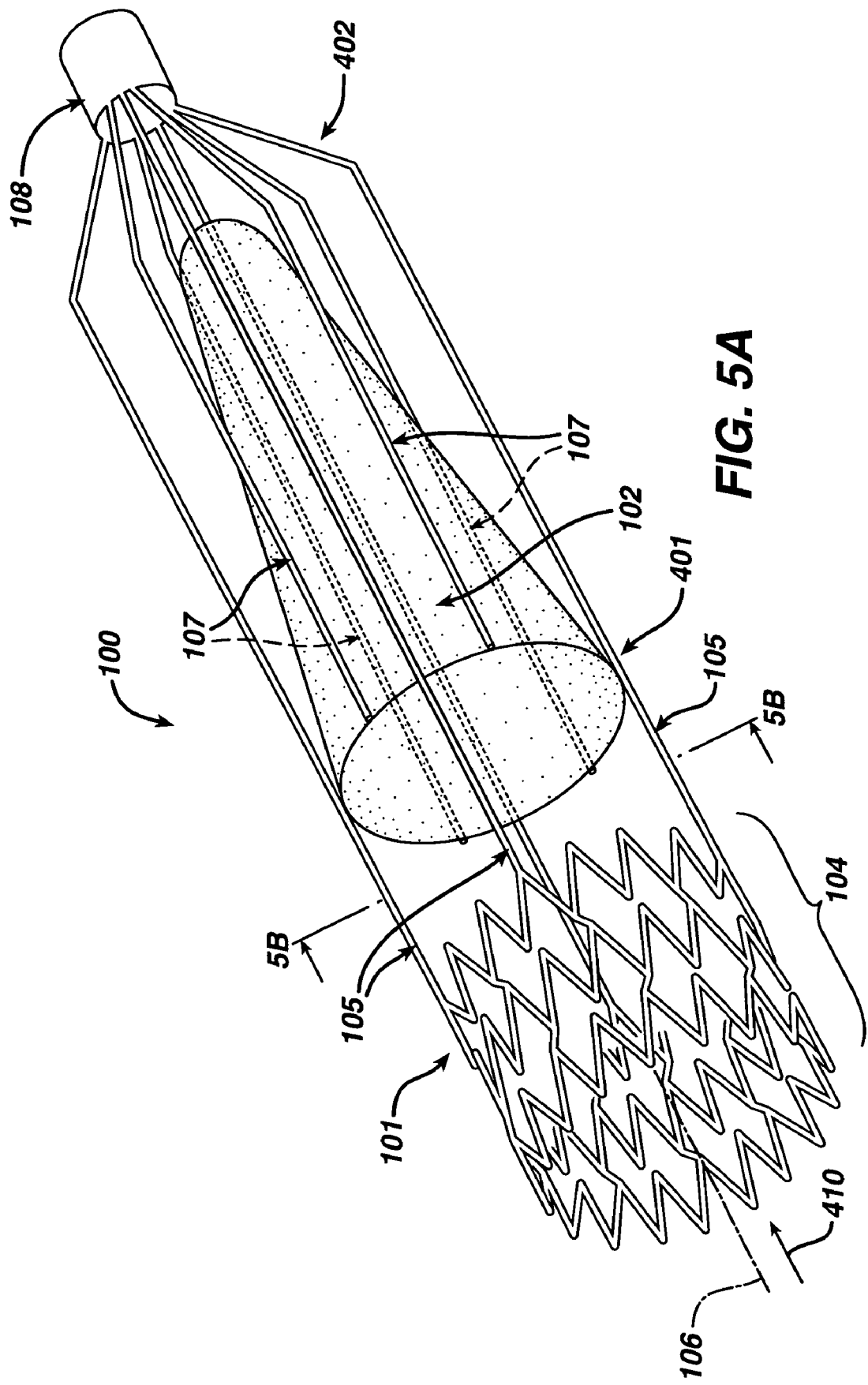
FIG. 5A is a perspective view illustrating one embodiment of the deployed prosthetic venous valve assembly in the closed position.
Figure 5B:
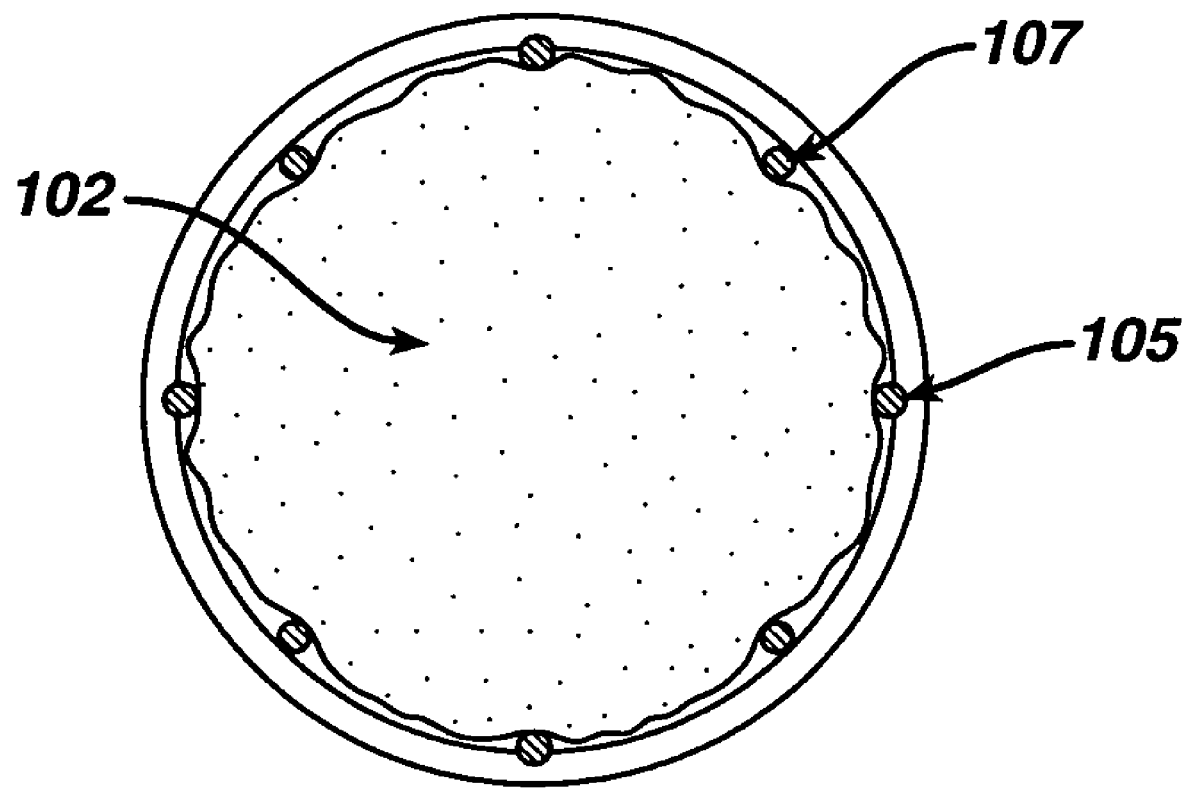
FIG. 5B is a section view illustrating one embodiment of the deployed prosthetic venous valve assembly in the closed position.

During retrograde flow, blood passes the leading edge along the first end 401 of the membrane assembly 102 and enters the membrane assembly 102 "cup". The cup quickly fills with the retrograde flowing blood, expanding the cup and opening the membrane assembly. As the membrane assembly 102 opens, the first end 401 of the membrane assembly 102 and the distal ends of the attached cantilever valve struts 107 are forced radially out toward the vessel wall, substantially occluding the vessel and thus reducing retrograde flow through the valve. In a preferred embodiment, the membrane assembly 102 will expand to a sufficient diameter to substantially seal against the inner vessel wall. FIGS. 5A and 5B show perspective and section views, respectively, illustrating one embodiment of the expanded (deployed) prosthetic venous valve assembly 100 in the closed position. As the term is used herein, closed means that the prosthetic venous valve 100 is configured to substantially prohibit retrograde blood flow 410 to pass through the valve. To accomplish this, the membrane assembly 102 is in an expanded position, substantially occluding the vessel.

In a preferred embodiment of the invention, the membrane assembly 102 is normally configured in the open position (membrane assembly 102 substantially collapsed), and only moves to the closed position (membrane assembly 102 substantially expanded) upon retrograde blood flow. This configuration minimizes interference with blood flow (minimized occlusion) and reduces turbulence at and through the valve. The cantilever valve struts 107 in this embodiment have an inferior radial stiffness, and provide a natural bias against the movement of the membrane assembly 102 to the closed position. This bias assists the valve membrane assembly 102 when returning to the open position.

Depending on the application, it may also be desirable for the bias towards opening the prosthetic valve 100 (collapsing the membrane assembly 102) be sufficiently high to commence collapsing the membrane assembly 102 before antegrade blood flow begins, i.e. during a point in time when the blood flow is stagnant (there is neither antegrade nor retrograde blood flow), or when minimal retrograde flow is experienced.

In other applications, it may be desirable to have the valve assembly 100 normally configured in the closed position (membrane assembly 102 in the expanded position), biased closed, and only open upon antegrade flow.

As earlier described, the membrane assembly 102 is made from a flexible membrane-like biocompatible material. The membrane assembly 102 can be woven, non-woven (such as electrostatic spinning), mesh, knitted, film or porous film (such as foam).

The membrane assembly 102 may be fixedly attached to the structural frame 101 (particularly cantilever valve strut 107) by many different methods, including attachment by means of a binder, heat, or chemical bond, and/or attachment by mechanical means, such as welding or suturing. In one embodiment, some of the membrane assembly 102, such as distal end 401, is slideably attached to the cantilever valve strut 107. Allowing the distal end 401 to slide along the cantilever valve strut 107 may allow or improve the opening and closing of the membrane assembly 102. The sliding movement may also assist the membrane assembly 102 cup when filling and emptying.

Figure 6A:
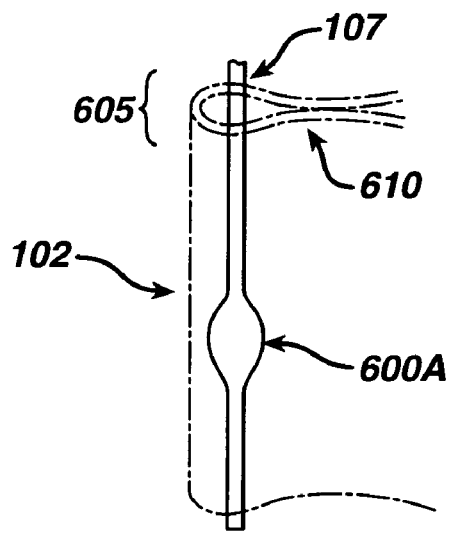
FIG. 6A is a perspective view illustrating a membrane limiting means according to one embodiment of the present invention.
Figure 6B:
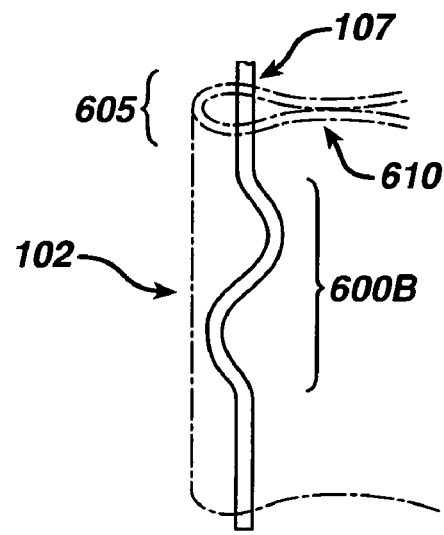
FIG. 6B is a perspective view illustrating a membrane limiting means according to one embodiment of the present invention.
Figure 6C:
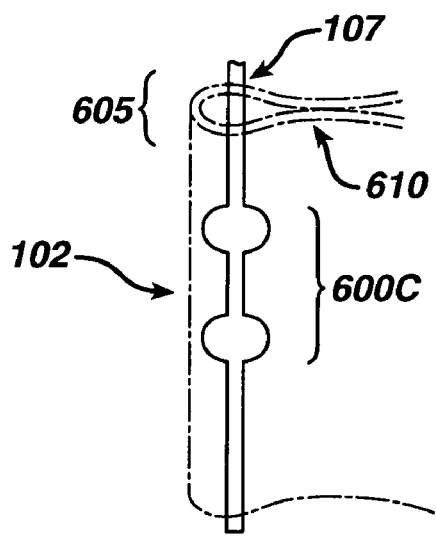
FIG. 6C is a perspective view illustrating a membrane limiting means according to one embodiment of the present invention.
Figure 6D:
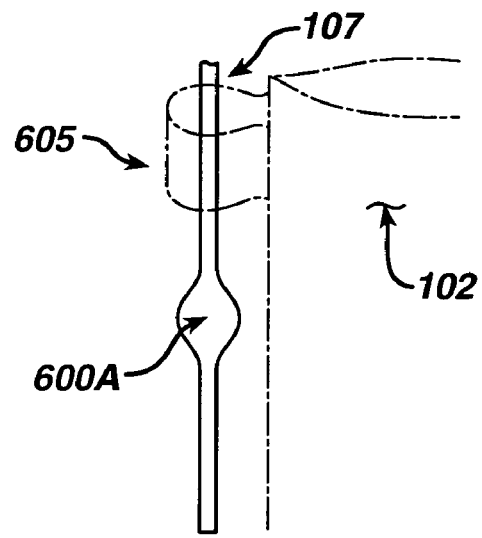
FIG. 6D is a perspective view illustrating a membrane limiting means according to one embodiment of the present invention.

In some applications, excessive sliding movement of the membrane assembly 102 is undesirable. In these embodiments, a limiting means may be integrated into the prosthetic valve 100 to limit the sliding movement of the membrane assembly 102. Examples of limiting means are shown in FIGS. 6A to 6C. In each embodiment a stop 600 (illustrated as stop 600A, 600B, and 600C in FIGS. 6A to 6C respectively) is integrated into the cantilever valve strut 107. The membrane assembly 102 is wrapped around the cantilever valve strut 107 and bonded to itself to form a loop collar 605. Alternatively, the loop collar 605 may be a separate biocompatible material wrapped around the cantilever valve strut and bonded to the membrane assembly 102. This separate loop collar 605 according to an alternate embodiment of the present invention is illustrated in FIG. 6D. The loop collar 605 must be sized to inhibit the distal end 401 of the membrane assembly 102 from sliding past the stop 600.

In FIG. 6A, the cantilever valve strut 107 has a thickened or "bulbous" section forming stop 600A. FIG. 6B illustrates an undulating stop 600B configuration. Similarly, FIG. 6C shows the stop 600C configured as a double bulbous section. It should be noted that the various configurations illustrated in FIGS. 6A through 6C are exemplary. One of ordinary skill in the art would understand that other configurations of stops may used.

It is important to note that the local delivery of drug/drug combinations may be utilized to treat a wide variety of conditions utilizing any number of medical devices, or to enhance the function and/or life of the device. Medical devices that may benefit from this treatment include, for example, the frame based unidirectional flow prosthetic implant subject of the present invention.

Accordingly, in addition to the embodiments described above, therapeutic or pharmaceutic agents may be added to any component of the device during fabrication, including, for example, the ESS fiber, polymer or coating solution, membrane tube, structural frame or inner and outer membrane, to treat any number of conditions. In addition, therapeutic or pharmaceutic agents may be applied to the device, such as in the form of a drug or drug eluting layer, or surface treatment after the device has been formed. In a preferred embodiment, the therapeutic and pharmaceutic agents may include any one or more of the following: antiproliferative/antimitotic agents including-natural products such as vinca alkaloids (i.e. vinblastine, vincristine, and vinorelbine), paclitaxel, epidipodophyllotoxins (i.e. etoposide, teniposide), antibiotics (dactinomycin (actinomycin D) daunorubicin, doxorubicin and idarubicin), anthracyclines, mitoxantrone, bleomycins, plicamycin (mithramycin) and mitomycin, enzymes (L-asparaginase which systemically metabolizes L-asparagine and deprives cells which do not have the capacity to synthesize their own asparagine); antiplatelet agents such as G(GP) ll$_b$/lll$_a$ inhibitors and vitronectin receptor antagonists; antiproliferative/antimitotic alkylating agents such as nitrogen mustards (mechlorethamine, cyclophosphamide and analogs, melphalan, chlorambucil), ethylenimines and methylmelamines (hexamethylmelamine and thiotepa), alkyl sulfonates-busulfan, nirtosoureas (carmustine (BCNU) and analogs, streptozocin), trazenes—dacarbazinine (DTIC); antiproliferative/antimitotic antimetabolites such as folic acid analogs (methotrexate), pyrimidine analogs (fluorouracil, floxuridine, and cytarabine), purine analogs and related inhibitors (mercaptopurine, thioguanine, pentostatin and 2-chlorodeoxyadenosine {cladribine}); platinum coordination complexes (cisplatin, carboplatin), procarbazine, hydroxyurea, mitotane, aminoglutethimide; hormones (i.e. estrogen); anticoagulants (heparin, synthetic heparin salts and other inhibitors of thrombin); fibrinolytic agents (such as tissue plasminogen activator, streptokinase and urokinase), aspirin, dipyridamole, ticlopidine, clopidogrel, abciximab; antimigratory; antisecretory (breveldin); anti-inflammatory: such as adrenocortical steroids (cortisol, cortisone, fludrocortisone, prednisone, prednisolone, 6α-methylprednisolone, triamcinolone, betamethasone, and dexamethasone), non-steroidal agents (salicylic acid derivatives i.e. aspirin; para-aminophenol derivatives i.e. acetominophen; indole and indene acetic acids (indomethacin, sulindac, and etodalac), heteroaryl acetic acids (tolmetin, diclofenac, and ketorolac), arylpropionic acids (ibuprofen and derivatives), anthranilic acids (mefenamic acid, and meclofenamic acid), enolic acids (piroxicam, tenoxicam, phenylbutazone, and oxyphenthatrazone), nabumetone, gold compounds (auranofin, aurothioglucose, gold sodium thiomalate); immunosuppressives:

(cyclosporine, tacrolimus (FK-506), sirolimus (rapamycin), azathioprine, mycophenolate mofetil); angiogenic agents: vascular endothelial growth factor (VEGF), fibroblast growth factor (FGF); angiotensin receptor blockers; nitric oxide donors; anti-sense oligionucleotides and combinations thereof; cell cycle inhibitors, mTOR inhibitors, and growth factor receptor signal transduction kinase inhibitors; retenoids; cyclin/CDK inhibitors; HMG co-enzyme reductase inhibitors (statins); and protease inhibitors.

While a number of variations of the invention have been shown and described in detail, other modifications and methods of use contemplated within the scope of this invention will be readily apparent to those of skill in the art based upon this disclosure. It is contemplated that various combinations or subcombinations of the specific embodiments may be made and still fall within the scope of the invention. For example, the embodiments variously shown to be prosthetic "venous valves" may be modified to instead incorporate prosthetic "heart valves" and are also contemplated. Moreover, all assemblies described are believed useful when modified to treat other vessels or lumens in the body, in particular other regions of the body where fluid flow in a body vessel or lumen needs to be controlled or regulated. This may include, for example, the coronary, vascular, non-vascular and peripheral vessels and ducts. Accordingly, it should be understood that various applications, modifications and substitutions may be made of equivalents without departing from the spirit of the invention or the scope of the following claims.

The following claims are provided to illustrate examples of some beneficial aspects of the subject matter disclosed herein which are within the scope of the present invention.

What is claimed is:

1. A prosthetic valve comprising:
a radially expandable structural frame defining a longitudinal axis, including an anchor structure having first and second open ends, a connecting member having first and second ends, the first end of the connecting member being directly attached to the second end of the anchor structure, and a cantilever valve strut having first and second ends, the first end of the cantilever valve strut being cooperatively associated with the second end of the connecting member and the second end of the cantilever valve strut being free to deflect in at least a radial direction from the longitudinal axis; and
a biocompatible membrane assembly having a substantially tubular configuration about the longitudinal axis, with a first open and a second closed end, the first end of the membrane assembly being attached along the second end of the cantilever valve strut.

2. The prosthetic valve of claim 1 wherein the anchor structure is formed from a lattice of interconnected elements, and has a substantially cylindrical configuration about the longitudinal axis.

3. The prosthetic valve of claim 1 wherein the structural frame comprises a material selected from the group consisting of stainless steel, tantalum, platinum alloys, niobium alloy, cobalt alloy, and nickel-titanium alloy.

4. The prosthetic valve of claim 1 wherein the structural frame comprises a polymer.

5. The prosthetic valve of claim 1 wherein the biocompatible membrane assembly is formed from a flexible membrane-like material.

6. The prosthetic valve of claim 5 wherein the membrane-like material is a biological material.

7. The prosthetic valve of claim 6 wherein the biological material is a vein.

8. The prosthetic valve of claim 5 wherein the membrane-like material is a synthetic material.

9. The prosthetic valve of claim 8 wherein the synthetic material is an elastomeric polymer.

10. The prosthetic valve of claim 8 wherein the synthetic material is a bioabsorbable material.

11. The prosthetic valve of claim 8 wherein the synthetic material further comprises a reinforcement fiber.

12. The prosthetic valve of claim 1 wherein at least a portion of the structural frame is coated with an agent.

13. The prosthetic valve of claim 12 wherein the agent coating contains a therapeutic agent.

14. The prosthetic valve of claim 12 wherein the agent coating contains a pharmaceutic agent.

15. The prosthetic valve of claim 12 wherein the agent coating comprises an agent-eluting layer.

16. The prosthetic valve of claim 1 wherein at least a portion of the membrane assembly is coated with an agent.

17. The prosthetic valve of claim 16 wherein the agent coating contains a therapeutic agent.

18. The prosthetic valve of claim 17 wherein the agent coating contains a pharmaceutic agent.

19. The prosthetic valve of claim 17 wherein the agent coating comprising an agent-eluting layer.

20. The prosthetic valve of claim 1 wherein at least a portion of the membrane assembly is impregnated with a therapeutic agent.

21. The prosthetic valve of claim 1 wherein at least a portion of the membrane assembly is impregnated with a pharmaceutic agent.

22. The prosthetic valve of claim 1 wherein the connecting member is a substantially straight member oriented in a direction substantially parallel to the longitudinal axis.

23. The prosthetic valve of claim 1 wherein the connecting member has a substantially helical shape about the longitudinal axis.

24. The prosthetic valve of claim 1 wherein the cantilever valve strut is a substantially straight member oriented in a direction substantially parallel to the longitudinal axis.

25. The prosthetic valve of claim 1 wherein the cantilever valve strut has a substantially helical shape about the longitudinal axis.

26. The prosthetic valve of claim 1 wherein the cantilever valve strut has a substantially sinusoidal shape oriented in a direction substantially parallel to the longitudinal axis.

27. The prosthetic valve of claim 1 wherein the tubular biocompatible membrane has a substantially constant diameter from the first to the second end.

28. The prosthetic valve of claim 1 wherein the tubular biocompatible membrane has a substantially conical shape.

29. The prosthetic valve of claim 1 wherein the structural frame further comprising a proximal collar attached to the second end of the connecting member and first end of the cantilever valve strut.

30. The prosthetic valve of claim 29 wherein the structural frame further comprises a centering leg cooperatively associated with the proximal collar.

31. The prosthetic valve of claim 29 wherein the structural frame further comprises a proximal anchor cooperatively associated with the proximal collar.

32. A prosthetic valve comprising:
a radially expandable anchor structure formed from a lattice of interconnected elements, and having a substantially cylindrical configuration with a first and a second open end and a longitudinal axis defining a longitudinal direction extending there between;

a connecting member having a first and a second end, the first end of the connecting member being directly attached to the second end of the anchor;

a cantilever valve strut having a first and a second end, the first end of the cantilever valve strut being cooperatively associated with the second end of the connecting member, and the second end of the cantilever valve strut being free to deflect in at least a radial direction from the longitudinal axis; and a biocompatible membrane assembly having a substantially tubular configuration with a first open and a second closed end, the first end of the membrane assembly being attached to the cantilever valve strut along the second end of the cantilever valve strut.

33. A prosthetic valve comprising:

a radially expandable anchor structure formed from a lattice of interconnected elements, and having a substantially cylindrical configuration with a first and a second open end and a longitudinal axis defining a longitudinal direction extending there between;

a collar located proximal to the radially expandable anchor;

a connecting member having a first and a second end, the first end of the connecting member being directly attached to the second end of the anchor and the second end of the connecting member being directly attached to the proximal collar;

a cantilever valve strut having a first and a second end, the first end of the cantilever valve strut being attached to the proximal collar and the second end of the cantilever valve strut being free to deflect in at least a radial direction from the longitudinal axis, the cantilever valve strut extending in a distal direction substantially parallel to the longitudinal axis; and a biocompatible membrane assembly having a substantially tubular configuration with a first open and a second closed end, the first end of the membrane assembly being attached to the cantilever valve strut along the second end of the cantilever valve strut.

\* \* \* \* \*